US007023605B2

(12) United States Patent  
Williams et al.

(10) Patent No.: US 7,023,605 B2
(45) Date of Patent: Apr. 4, 2006

(54) DIGITAL MICROMIRROR DEVICE HAVING A WINDOW TRANSPARENT TO ULTRAVIOLET (UV) LIGHT

(75) Inventors: Roy E. Williams, Collierville, TN (US); Brian M. Callies, Cordova, TN (US)

(73) Assignee: Memphis Eye & Cataract Associates Ambulatory Surgery Center, Memphis, TN (US)

( * ) Notice: Subject to any disclaimer, the term of this patent is extended or adjusted under 35 U.S.C. 154(b) by 74 days.

(21) Appl. No.: 10/395,660

(22) Filed: Mar. 24, 2003

(65) Prior Publication Data

US 2004/0190281 A1    Sep. 30, 2004

(51) Int. Cl.
*G02B 26/00* (2006.01)
(52) U.S. Cl. ............... 359/290; 359/291; 359/292; 359/293
(58) Field of Classification Search ............... 359/290, 359/291, 292, 298, 293, 297, 299
See application file for complete search history.

(56) References Cited

U.S. PATENT DOCUMENTS

| 5,624,437 | A | 4/1997 | Freeman et al. ............... 606/12 |
| 6,242,136 | B1 | 6/2001 | Moore et al. ................... 430/5 |
| 6,394,999 | B1 | 5/2002 | Williams et al. ............... 606/5 |
| 6,413,251 | B1 | 7/2002 | Williams ....................... 606/5 |
| 6,441,359 | B1* | 8/2002 | Cozier et al. ............... 250/216 |
| 6,720,206 | B1* | 4/2004 | Choi ........................... 438/114 |
| 6,755,554 | B1* | 6/2004 | Ohmae et al. .............. 362/293 |
| 2002/0016629 | A1 | 2/2002 | Sandstedt et al. .......... 623/6.11 |
| 2003/0101562 | A1* | 6/2003 | Hanna et al. ................. 29/412 |
| 2003/0210452 | A1* | 11/2003 | Haskett et al. .............. 359/290 |

OTHER PUBLICATIONS

"Photorefractive Keratectomy: A Technique for Laser Refractive Surgery" by Munnerlyn et. al., J Cataract Refract Surg, vol. 14, Jan. 1988.
"Objective Measurement of Wave Aberrations of the Human Eye with the Use of a Hartmann-Shack Wave-front Sensor" by Junzhong Liang, et al., Optical Society of America, vol. 11, No. 7, Jul. 1994.
"Digital Light Processing™ for High-Brightness, High-Resolution Applications" by Larry Hornbeck, Texas Instruments, Electronic Imaging, San Jose, California, El '97, Projection 2, vol. 11, No. 7, Jul. 1994.
"Advanced Materials for Optoelectronic Packaging" by Carl Zweben, Advanced Theramal Materials Cosnultant, Devon, Penn, Sep. 1, 2002, downloaded from web Site www.e-insite.net.
"Hermetic Lids for Electronic Packaging", Williams Advanced Materials 2002, downloaded from web site www.williams-adv.com.
"Visi-Lid ™Hermetic Window Assemblies" by Micahel Zasowski, Williams Advanced Materials 2002, downloaded from web site www.williams-adv.com.

* cited by examiner

Primary Examiner—Ricky L. Mack
Assistant Examiner—Brandi Thomas
(74) Attorney, Agent, or Firm—Gordon & Jacobson, P.C.

(57) ABSTRACT

A UV-transmissable window assembly for a DMD device includes a UV-transmissable glass window provided in a frame. The window and frame are bonded together to preferably effect a hermetic seal therebetween. Optical coatings specific to the intended wavelength of light transmission are applied to the inner and outer surfaces of the glass window to reduce reflection and increase light transmission therethrough. The window assembly, and DMD provided with the same, is adapted for excellent transmission of ultraviolet light, even at the deep ultraviolet portion of the spectrum. The DMD window assembly has application in the medical arts, both surgery and device manufacture, in the production of integrated circuits (IC), and in other optical lithography applications, among other fields.

30 Claims, 17 Drawing Sheets

DIGITAL MICROMIRROR DEVICE HAVING A WINDOW TRANSPARENT TO ULTRAVIOLET (UV) LIGHT

BACKGROUND OF THE INVENTION

1. Field of the Invention

This invention relates broadly to optical systems. Particularly, this invention relates to micro-electro-mechanical-systems (MEMS) having optically reflective and transparent elements, and more particularly, to such systems wherein the optically transparent elements are transparent to ultraviolet light wavelengths.

2. State of the Art

The correction of abnormal human vision has progressed rapidly over the past few years. Although eyeglasses and contact lenses are still the dominant approach for correcting vision, newer techniques involving the reshaping of the cornea, and the replacement or supplement of the internal human lens, are providing more precise correction. To correct vision via the reshaping of the human cornea, precision surgical scalpels or lasers are used. Although still used, radial keratotomy (RK), which uses a surgical scalpel, is quickly being replaced by photorefractive keratectomy (PRK) and laser in-situ keratomileusis (LASIK), which use lasers. The laser refractive surgery field has exploded over the past few years with many new lasers and algorithms to correct human vision. Systems are now using laser wavelengths from the deep-ultraviolet to the infrared to change the shape of the cornea in a calculated pattern, which makes it possible for the eye to focus properly.

Artificial intraocular lenses (IOLs), which replace the human lens, usually due to cataract formation or lens damage, also provide very good vision correction, but, like contact lenses, which can offer "broad" spherical and astigmatic correction, they are limited in the precision of their corrective power. There are also supplemental refractive-IOLs which are inserted in the anterior chamber of the eye, the space between the iris and the cornea, while leaving the original lens intact. Light adjustable IOLs which are able to be altered outside the eye, or within the eye after implantation, thus allowing more custom-fit and more precise corrective power, are now undergoing research. Such an IOL is described in U.S. Pat. Application 2002/0016629 entitled "Application of Wavefront Sensor to Lenses Capable of Post-Fabrication Power Modification", which is incorporated by reference herein in its entirety. Mid-UV to deep-UV lasers are used to alter these IOLs to provide varying refractive powers.

Finer, more precise measurements of human eye abnormalities have also been improving over the past several years. As these measurements have been improving, the industry has searched for ways to generate more custom corrections to the eye or to the IOL. The Digital Micromirror Device™ (DMD™), a micro-electro-mechanical-system (MEMS) semiconductor device consisting of hundreds of thousands of micromirrors, is an ideal device to deliver the custom laser beam pattern more precisely. The use of the DMD™ with respect to laser eye surgery is described in detail in co-owned U.S. Pat. No. 5,624,437, entitled "High Resolution, High Speed, Programmable Laser Beam Modulating Apparatus for Microsurgery", U.S. Pat. No. 6,394,999 entitled "Laser Eye Surgery System Using Wavefront Sensor Analysis to Control Digital Micromirror (DMD) Mirror Patterns", and U.S. Pat. No. 6,413,251 entitled "Method and System for Controlling a Digital Micromirror Device for Laser Refractive Eye Surgery", all of which are hereby incorporated by reference herein in their entireties. Current, commercially-available DMD devices are designed to deliver visible wavelengths (from 400-nm to 750-nm), however, and cannot be used to deliver a large range of UV energy because of their protective window, which environmentally guards the micromirrors. UV energy can be categorized by wavelength according to physical definitions: extreme UV (EUV)(10 nm to 100 nm), vacuum UV (VUV) (10 nm to 200 nm, with recognition that VUV overlaps EUV), far or deep UV (DUV)(200 nm to 300 nm), and near UV (NUV)(300 nm to 400 nm). In addition, UV energy can be categorized by wavelength according to photobiologic definitions: UV-C (100 nm to 280 nm) which overlaps far and deep UV, UV-B (280 nm to 315 nm) which overlaps far and near UV and is also termed mid-UV, and UV-A (315 nm to 400 nm) which overlaps deep and near UV and which is also termed near-UV for photobiologic purposes.

Refractive Surgery: Corneal Reshaping by Laser and the Use of the DMD

Initial systems approved by the FDA for corneal reshaping implement the refractive correction by delivering beam-shaped laser energy based on first-order approximations of refraction from a single spherical surface. These systems implement a "broadbeam" approach, whereby the laser beam is shaped by a motorized iris (myopia and hyperopia) and motorized slit (astigmatism) based on profiles derived through Munnerlyn's derivation, as discussed in C. R. Munnerlyn, et al., "Photorefractive keratectomy: a technique for laser refractive surgery," *J. Cataract Refract. Surg.* 14, 46–52 (1988). Typical systems using this approach on the market are VISX and Summit. More than one million eyes have been treated in this manner. This system is limited, however, as it treats a broad area of the cornea all at one time. Eye topography maps and more recently, wavefront analysis, reveal the eye has many minute variations across the cornea. See, e.g., J. Liang, et al., "Objective measurement of wave aberrations of the human eye with the use of a Hartmann-Shack wave-front sensor," *J. Opt. Soc. Am. A*, Vol. 11, No. 7, 1949–1957 (1994). Referring to FIGS. 1(*a*) and 1(*b*), the broadbeam laser approach cannot correct these minute variations.

The latest systems being introduced to the market are based on scanning a small laser spot (typically 0.5-mm to 1.0-mm diameter), or a combination of different sized spots, across the cornea in a predetermined pattern to achieve refractive corrections, and are termed "scanning spot systems". These scanning spot systems differ in that they are more flexible than the broadbeam approach. Referring to FIG. 2, with the control of a small spot 10, one can shape different areas of the cornea 12 independently of other areas. These techniques allow for a more general pattern to be applied to the cornea. Typical systems using the scanning spot approach are VISX, Autonomous Technologies, LaserSight, and SurgiLight.

However, there are several problems with the scanning spot approach when compared with the broadbeam approach but the flexibility offered appears to outweigh these. Some problems include longer refractive surgery time (speed), safety, tracking and surface roughness, which are discussed in more detail as follows.

With respect to longer refractive surgery times, the scanning spot is a slower approach since a small spot (typically 1-mm diameter) has to be moved over a wide surface (up to 10-mm for hyperopia). The broadbeam approach treats the entire cornea for each laser pulse, or treatment slice. The scanning spot system must deliver several hundred spots per treatment slice; thus, treatment times can increase.

With respect to safety, the broadbeam laser is inherently safe from a treatment interruption standpoint because the cornea is treated symmetrically for each pulse (the iris represents a circle and the slit represents a rectangle so that every point on the cornea is treated the same for each laser pulse). If the procedure is interrupted, you are guaranteed to have some symmetrical spherical or cylindrical correction, which can be continued easily. The scanning spot, with its small spot size, cannot cover the entire corneal surface with one laser pulse so that if an interruption occurs, there is no guarantee of a symmetrical etch at that point.

With respect to tracking, in the scanning spot system, the eye needs to be tracked in order to deliver the spot to the correct point on the cornea as the eye moves. This is not as much of a problem in the broadbeam system as a broader area is treated with each pulse.

With respect to surface roughness, laser spot overlap tends to create roughness in the resulting etch. While it is necessary to overlap spots to provide complete coverage for a given ablation zone, regions of overlap will be ablated at twice the etch depth per pulse. The smoothness of the ablated volume is dependent on the spot overlap and to a lesser extent, the ratio of spot diameter and ablation zone diameter. This problem is not seen in the broadbeam approach.

More recently, eye contour topography is being used to more accurately provide refractive measurements. Current FDA-approved refractive laser systems do not directly use eye-modeling systems, such as corneal topographers or wavefront sensors, to create the correct treatment profile for the patient's eye. The topographic map is used indirectly by the surgeon for optimizing the treatment plan (diopter correction and astigmatic axis). There are systems currently going through FDA trials that do use corneal topographic surface data to directly guide the laser treatment algorithm. This is accomplished using some type of scanning laser spot, as current broadbeam laser refractive surgery systems cannot provide the laser beam detail required to use the topographic map data. Each eye is individually analyzed as to its contour before ablation is applied. The idea here is to take into account the varying degrees of curvature and height variations across the corneal surface, as opposed to assuming a spherical surface as is currently done in broadbeam systems. Once these curvatures, or powers, are determined by eye topography, e.g., by using a system sold by Keratron, Orbtek, or Zeiss-Humphrey, they can be considered within the refraction correction derivation (as described by Munnerlyn) to create a customized ablation pattern for each individual eye. These ablations must be implemented by a scanning spot system, or better yet a DMD approach, as individual areas must be treated differently than other areas. Previously incorporated U.S. Pat. Nos. 5,624,437 and 6,413,251 discuss the DMD approach. Even this approach is limited in that only aberrations measured on the corneal surface are included in the refractive correction derivation.

The optimum approach to date uses the recent introduction of wavefront sensing analysis of the eye. With this new technology, a very powerful set of tools to correct the eye corneal surface is provided. Wavefront sensing provides an overall refractive analysis of the entire eye optical system, e.g., taking into account the cornea, the lens, the vitreous and the retina. The result of a wavefront sensor analysis yields a waveform model that represents a nearly perfect refraction measurement. This provides a superior analysis of the eye versus the current topography systems that only analyze the cornea. Wavefront data may be used to drive a scanning spot system, but it still encompasses the problems discussed before. However, it is directly compatible with the DMD approach due to the digital nature of the wavefront sensor analysis. This wavefront sensor-DMD approach is discussed in detail in previously incorporated U.S. Pat. No. 6,394,999.

Refractive Surgery: Light Activated IOLs and the Use of the DMD

Modern cataract surgery, in which the cataract is actually extracted from the eye, was introduced by Jacques Daviel in Paris in 1748. Samuel Sharp of London introduced the concept of intracapsular cataract surgery in 1753 by using pressure with his thumb to remove the entire lens intact through an incision. Small suction cups (erysiphakes) were introduced for this purpose in 1902 as well as various capsular forceps to grasp the lens for removal. Henry Willard Williams of Boston first described the use of sutures for cataract surgery in 1867. In the 1840s general anesthesia was introduced for surgical procedures, however it was not until 1884 that anesthesia in the form of eye drops (cocaine) was developed, obviating the hazards of general anesthesia and its postoperative complications. After Harold Ridley introduced the intraocular lens in England in the 1940s, efficient and comfortable visual rehabilitation became possible following cataract surgery.

The intraocular lens, or IOL, is a permanent plastic lens implanted inside the eye to replace the crystalline lens. In 1957 Barraquer of Spain used alpha-chymotrypsin to enzymatically dissolve the zonules for removal of the lens. Cryosurgery was introduced by Krawicz of Poland in 1961 to remove the lens with a tiny probe that could attach by freezing a small area on the surface of the cataract. In the late 1960s Charles Kelman of New York developed a technique for emulsifying the lens contents using ultrasonic vibrations and aspirating the emulsified cataract. In recent decades, there has been a rapid evolution of designs, materials, and implantation techniques for intraocular lenses, making them a safe and practical way to restore normal vision at the time of surgery.

More recently, designs have been implemented to provide accommodation with an IOL. Such attempts include diffractive multifocal lenses, flexible (fluid-filled) lenses, multi-element designs and hinged optics. These IOLs still only offer "broad" fixed power correction (both spherical and astigmatic), although they do offer some accommodative power.

Even more recently, light-activated IOLs have been proposed. These optical elements have a refraction modulating composition dispersed in a polymer matrix. The refractive modulating composition is capable of stimulus-induced polymerization, e.g., a UV light stimulus (longer wavelength UV: 325-nm to 340-nm range). In this way, an optical measurement (e.g., topography, wavefront, etc.) of the eye can be made followed by inducing an amount of polymerization of the refractive modulating composition, wherein the amount of polymerization is determined by the optical measurement. Thus, the varying degrees of curvature and height variations across the corneal surface can be taken into account, as opposed to assuming a simple spherical surface. Currently, collimated light from a Xe:Hg arc lamp (340-nm through a 1-mm photomask), or collimated light from a He:Cd laser (325-nm, 1-mm beam diameter), is used to activate and stabilize (or "lock in") the refractive modulating composition. To polymerize the entire IOL, the 1-mm photomask, or 1-mm laser beam, must be moved or scanned across the IOL, as described in U.S. Pat. Application 2002/0016629 A1 entitled "Application of Wavefront Sensor to Lenses Capable of Post-Fabrication Power Modification", which is incorporated by reference herein in its entirety. Scanning the small masks or small diameter laser beams across the IOL present the same problems as described in the scanning spot approach to corneal tissue reshaping discussed above. Therefore, when coupled to a proper collimated broadbeam arc lamp, or a broadbeam laser, this technique is directly compatible with the DMD approach due to the digital nature of the topographic or wavefront sensor analysis, and since it can provide larger, custom laser beam patterns more precisely.

The DMD Problem for Ultraviolet Wavelengths

From the above discussion, it is apparent that the DMD is ideally suited to provide the necessary laser delivery control, in both the corneal reshaping application and the IOL activation application, to obtain the finer resolution and custom laser beam patterns required by the more advanced measurement techniques. To date, however, there has not been a commercially-available DMD to provide delivery of the excimer wavelength used in laser refractive surgery (193-nm) or the wavelengths used in the light-activated IOL approach (325-nm to 340-nm). The shortest optimized wavelength able to be delivered by a manufactured, but still experimental DMD is 365-nm, far above the 193-nm necessary to etch the cornea in the laser refractive surgery area.

Referring to FIG. 3, it is noted that at 325-nm, a wavelength used in the IOL application, only about 83% of the light is transmitted through the UV-coated DMD window in a single pass. Moreover, with the DMD device, the light that strikes the mirrors must make two passes through the window; that is, the light must travel through the window first, reflect from the mirrors and travel through the window again to exit the device. This means that only about 69% (0.83×0.83) of the original 325-nm light returns from the DMD, assuming 100% reflection from the DMD mirrors, or a loss of 31% due to the window alone. At 340-nm, only about 91% of the light is transmitted in a single pass. Thus, for 340-nm, only about 83% (0.91×0.91) of the original 340-nm light returns from the DMD, assuming 100% reflection from the DMD mirrors, or a loss of 17% due to the window alone. The result of this loss is that the laser source must operate at higher energy output levels, which also increases damage to the beam shaping and delivery optics. Furthermore, there are other losses associated with the optics that are required to shape, homogenize, and deliver the laser beam (typically 45% to 60% loss). Additional losses result from damage to the optical coatings as a result of use.

To further illustrate the window losses, consider an example from U.S. Pat. Application 2002/0016629 A1, where a 1-mm diameter, 325-nm He—Cd laser beam with an energy density of 257 $mJ/cm^2$ is required to induce the refractive modulating composition polymerization. To cover the entire 6.35-mm IOL with the laser beam at one time, as would be necessary using a DMD to activate the refractive modulating composition, this would require 81 mJ of energy at the IOL. With the above window losses of 31% at 325-nm, coupled to the typical losses of 50% for the beam shaping and delivery optics, this would require over 500-mJ from the laser, while operating from two minutes to ten minutes. Thus, it would be advantageous to have a deep UV window as lossless as possible to keep the laser energy requirement down.

As another example, consider the energy density required to etch corneal tissue. Although energy densities vary from system to system, a typical value is 160 $mJ/cm^2$. A current commercially-manufactured, but experimental, DMD will not work for the laser refractive surgery wavelengths of between 190-nm to 250-nm (typically 193-nm) because as seen from FIG. 3, the UV-coated window covering the mirrors of the DMD has a 0% optical transmission below 250-nm. Thus, the only way to implement the DMD for this application is to use a window designed for these deep-UV wavelengths. For a typical 6-mm spot used in laser refractive surgery, an energy density of 160 $mJ/cm^2$ requires 45-mJ. For a 10-mm spot, used to correct hyperopia, 125-mJ is required. Typical treatment times for broadband lasers range from a few seconds to one minute. Thus, the deep UV window needs to be as lossless as possible to keep the laser energy requirement down.

Another significant problem that exists with current DMD window designs is the reflections from the window surfaces, particularly on the DMD mirror side of the window. If the window and its coating are not optimized for the wavelength used, reflections can bounce back and forth from the inside of the window to the mirrors giving rise to "ghost images" that can cause interference problems resulting in incorrect patterns being delivered.

Current DMD windows assemblies are constructed of a Kovar® (ASTM-F-15) metal alloy frame and a borosilicate glass window. This combination is a common glass-ceramic sealing systems for protecting semiconductors (e.g., EPROMS) from a local environment. Kovar® is a low-expansion alloy whose chemical composition is controlled within narrow limits to assure precise uniform thermal expansion properties.

The most common borosilicate glass used in the current DMD application is Corning 7056. Corning 7056 glass works well for the visible light spectrum DMD application because it passes visible light well and its coefficient of thermal expansion (CTE) is very close to Kovar® (Corning 7056: $5.15 \times 10^{-6}/°$ C. versus Kovar®: $5.2 \times 10^{-6}/°$ C.). This allows a glass-to-metal hermetic seal when both are heated to nearly 1000 degrees Celsius. The traditional hermeticity definition is based on the Helium Fine Leak Test (mil-std 803 or JEDIC-JESD22-A109-A) where the value must be $5 \times 10^{-8}$ atm-cc/s helium or better. The hermetic seal is formed by heating both the glass and metal until a wetting of the metal by the glass occurs, followed by the development of a chemical bond or some mechanical interlocking, thus maintaining the seal. The base transmission spectrum of Corning 7056 is shown in FIG. 4. By applying appropriate anti-reflection (AR) coatings to the glass, the transmission spectrums of FIG. 3 are achieved. Note the optical transmission can be shifted lower to handle the near-UV wavelengths, but this degrades part of the visible spectrum. Finally, note again that this glass will not pass deep-UV to mid-UV wavelengths very effectively. Instead a different material, such as fused silica, is required.

Fused silica is one of the most common materials used in the deep-UV to mid-UV applications. Fused silica is a polycrystalline, isotropic material with no crystal orientation. Its physical, thermal, dielectric and optical properties are uniform in all directions of measurement. There are special grades of fused silica, termed excimer grade fused silica, made especially for the above applications. Unfortunately, the CTE of fused silica ($0.55 \times 10^{-6}/°$ C.) is not very close to the CTE of Kovar® ($5.2 \times 10^{-6}/°$ C.) (differing by substantially an order of magnitude), and thus during the manufacturing process, and in the post-manufacturing environment, as temperatures vary, the hermetic seal between the two is not maintained. This allows the outside environment into the hermetically-sealed DMD semiconductor space and this becomes detrimental to the micromirrors behind the window causing them not to function properly. One of the most common problems is that the mirrors stick and do not respond to commands.

There are three additional problems with respect to current DMD mirror design. First, the current commercially-available DMD device uses bare aluminum mirrors to reflect the incoming light. Uncoated, or bare, aluminum provides about an 85% absolute reflectance from 200-nm to 2000-nm. This reflectance increases as wavelengths move into the visible area (about 90% averaged over 400-nm to 750-nm), as in the main application of the currently-manufactured DMD devices, and decreases as wavelengths move below 200-nm (e.g., about 84–86% for 193-nm and about 65–70% for 157-nm). Therefore, the uncoated aluminum DMD mirrors provide less than 85% reflectance, or greater than a 15% loss, for certain UV applications.

Second, the UV energy that strikes the mirrors also gradually erodes the mirrors, which damages or deforms them. This negatively affects the laser energy pattern that is delivered to the target.

Third, the incoming UV energy will travel between the mirrors and impinges on the underlying semiconductor control structure behind the mirrors. This can lead to degradation of the DMD device.

SUMMARY OF THE INVENTION

It is therefore an object of the invention to provide a window assembly for a DMD that is substantially transparent to ultraviolet light.

It is another object of the invention to provide a window assembly for a DMD that is substantially transparent to wavelengths of light in the near, deep, and vacuum ultraviolet portions of the spectrum.

It is a further object of the invention to provide a window assembly for a DMD that has minimal reflectance.

It is also an object of the invention to provide a window assembly for a DMD that includes a window hermetically sealed to a frame.

It is an additional object of the invention to provide a DMD having a window suitable for applications which use light at ultraviolet wavelengths, and particularly in the near, deep and vacuum ultraviolet wavelength portions of the spectrum.

It is yet another object of the invention to provide a DMD for use with ultraviolet wavelengths, wherein the DMD window seals are not subject to outgassing problems and thus will not negatively affect the DMD mirrors or the control electronics.

It is yet a further object of the invention to provide a DMD window construction suitable for use with ultraviolet light and which may be safely cleaned with typical optical cleaning solutions, such as acetone and methanol.

It is yet an additional object of the invention to increase UV light transmission and reflection through the entire DMD system.

In accord with these objects, which will be discussed in detail below, a near-, deep-, and vacuum-UV wavelength window assembly for a DMD device, and a DMD device incorporating the same, is provided. The window assembly includes a fused silica glass window provided in a high temperature metal alloy frame. In a preferred embodiment, the fused silica glass window is an Argon fluoride grade fused silica, and the frame is made from a nickel-cobalt-iron alloy such as Kovar®. A lead/silver alloy bonding material interface is provided at the juncture of the window of the frame and provides a hermetic seal between the alloy and the glass. Optical coatings specific to the intended wavelength of light transmission are applied to the inner and outer surfaces of the glass window to reduce reflection and increase light transmission therethrough.

The resultant window assembly, and DMD provided with the same, is adapted for excellent transmission of ultraviolet light throughout vacuum-UV, deep-UV and near-UV wavelengths. A DMD with a window adapted for such ultraviolet light transmission has application in the medical arts, in both surgery and the manufacture of medical devices such as intraocular lenses, contact lenses or eyeglasses, or to selectively alter the bio-response of a surface; in the production of integrated circuits (IC) and in other optical lithography applications (such as polymer arrays); the custom manufacture of industrial lenses; micromachining (e.g., microhole drilling, selective thin-film removal, and milling); and precise surface roughening of material, among other fields.

Additional objects and advantages of the invention will become apparent to those skilled in the art upon reference to the detailed description taken in conjunction with the provided figures.

BRIEF DESCRIPTION OF THE DRAWINGS

Prior art

Prior art

Prior art

Prior art

Prior art

FIG. 7(a) is for a 16-micron. mirror configuration, and FIG. 7(b) is for a 13.7-micron mirror configuration;

DETAILED DESCRIPTION OF THE PREFERRED EMBODIMENTS

Figures 1A, 1B:
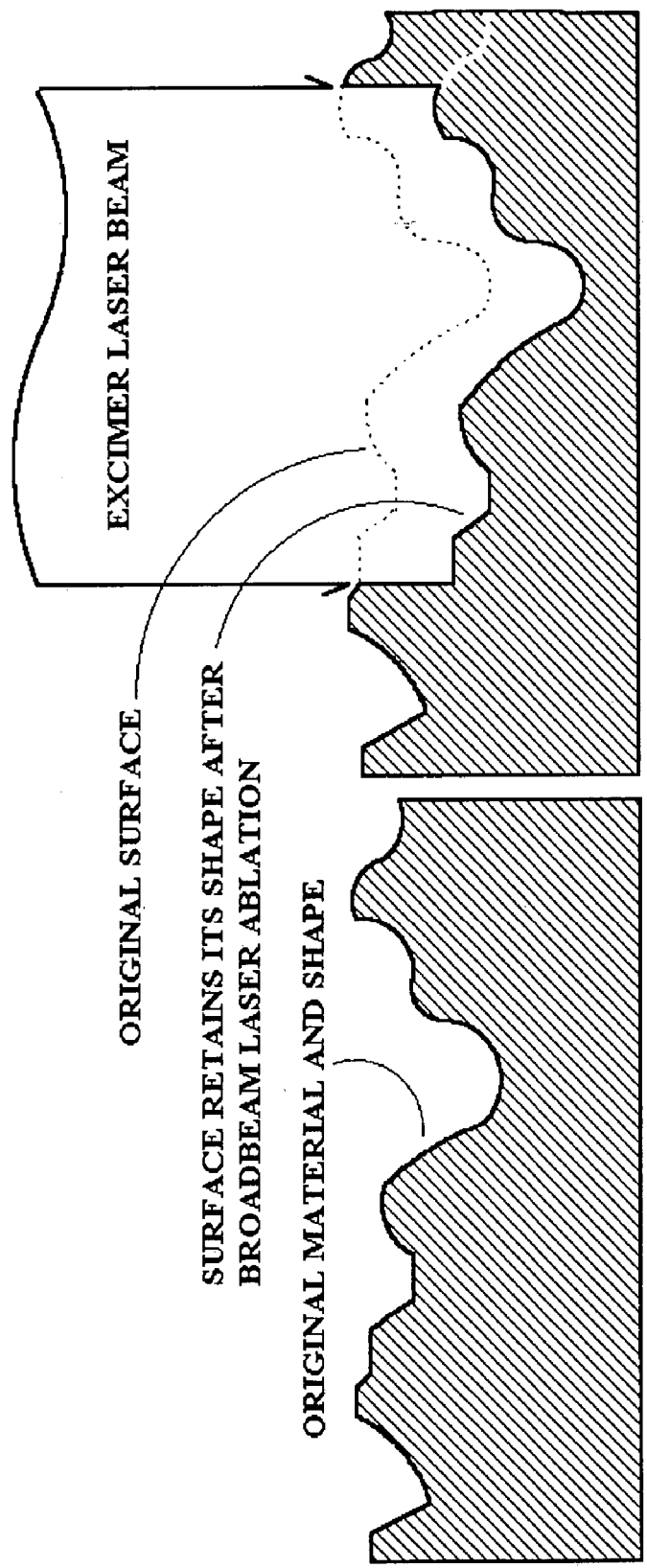
FIG. 1(a) illustrates minute variations on a corneal surface.
FIG. 1(b) illustrates a broadbeam laser ablation of the corneal surface of FIG. 1(a), showing how minute variations of the surface are maintained after broadbeam laser ablation.
Figure 2:
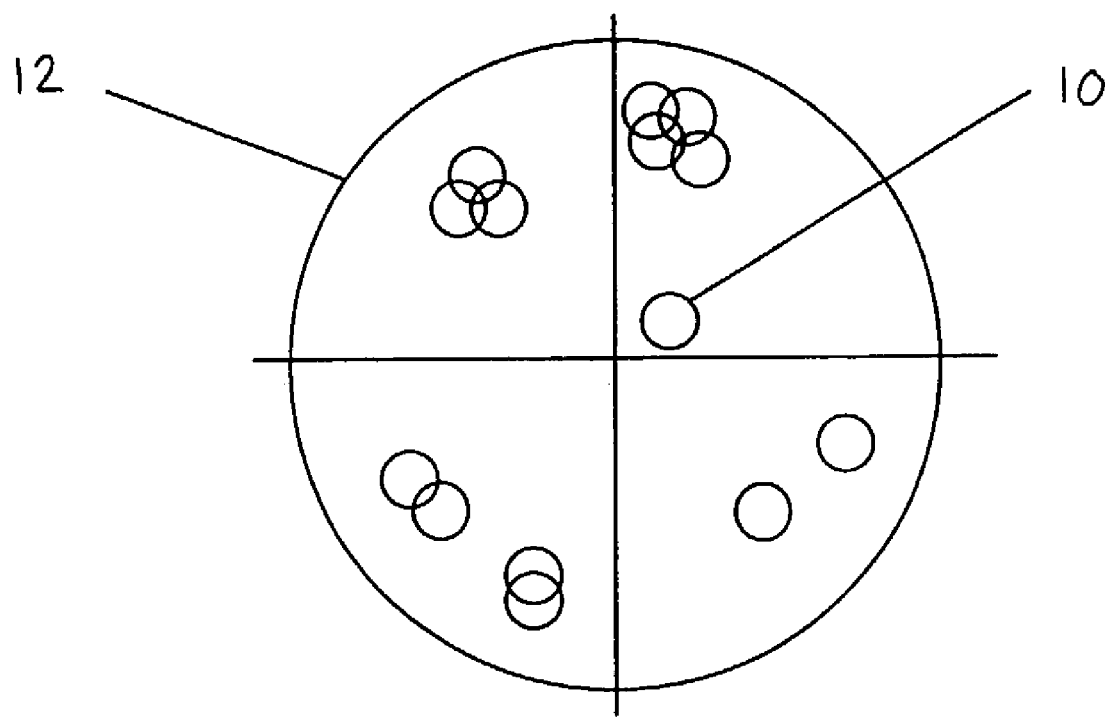
FIG. 2 illustrates a scanning spot approach showing the flexibility of firing many small spots.
Figure 3:
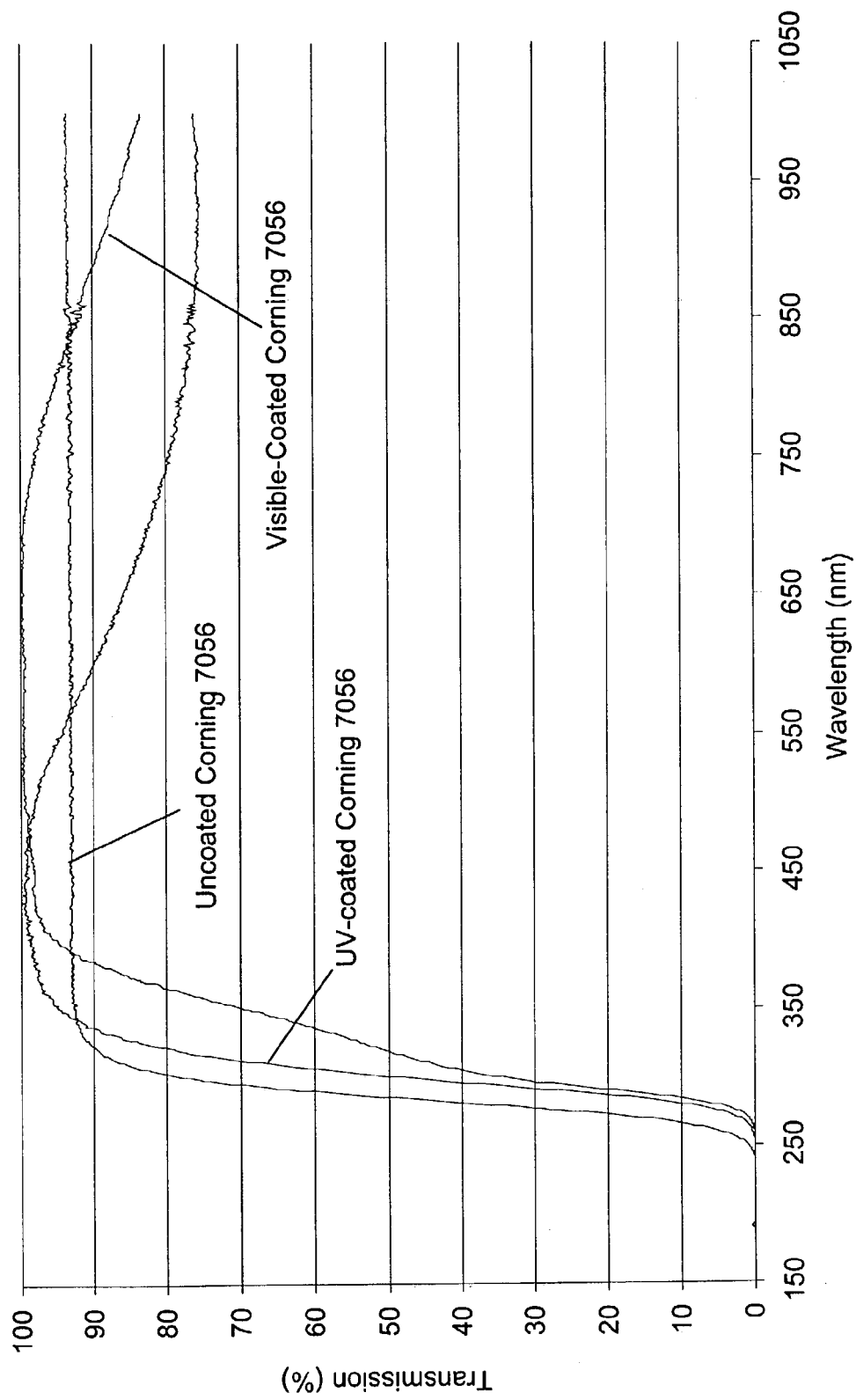
FIG. 3 shows a graph of current, commercially-available DMD window transmission spectrums.
Figure 4:
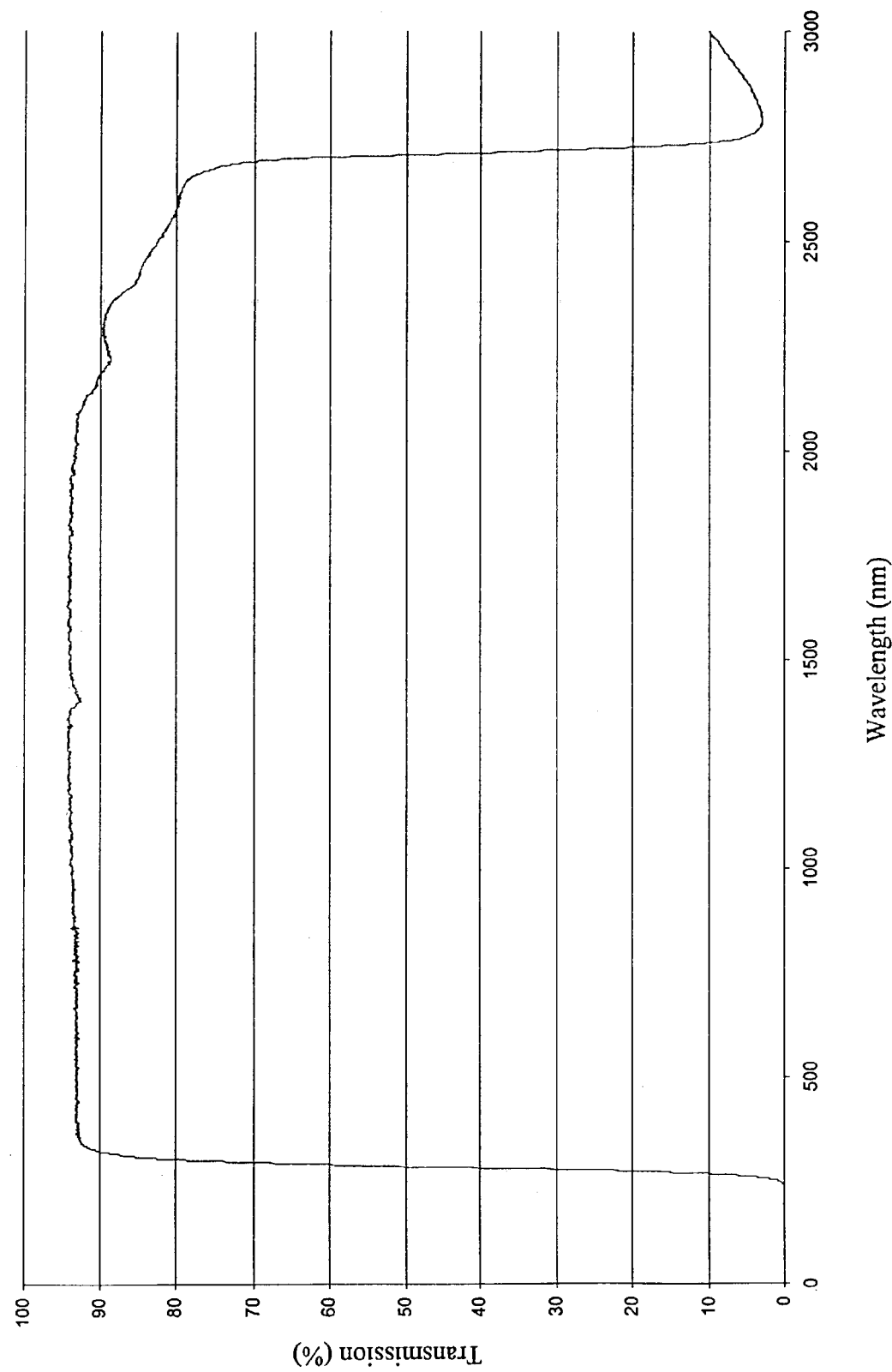
FIG. 4 shows a transmission spectrum of borosilicate glass used in current DMD application.
Figure 5A:
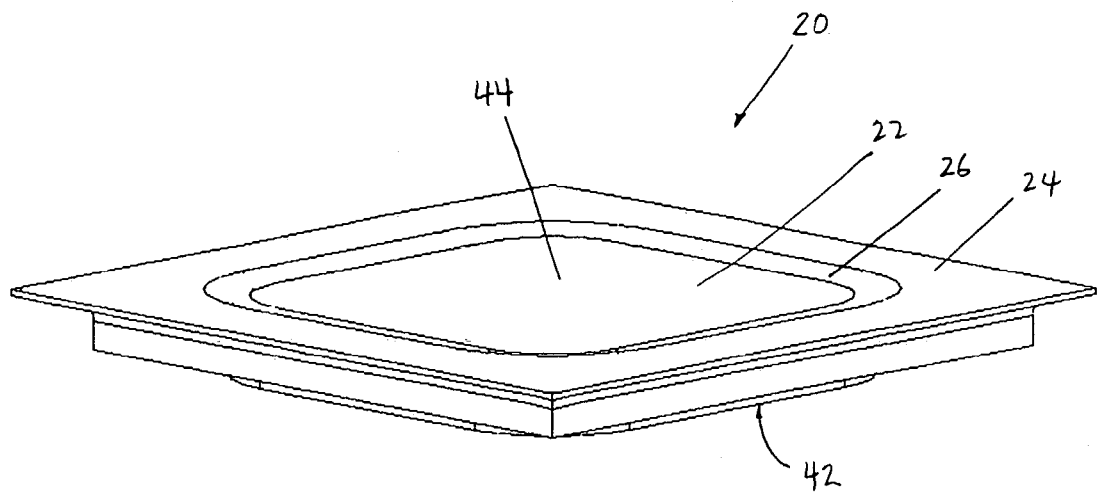
FIG. 5(a) is a bottom perspective view of a window assembly according to the invention.
Figure 5B:
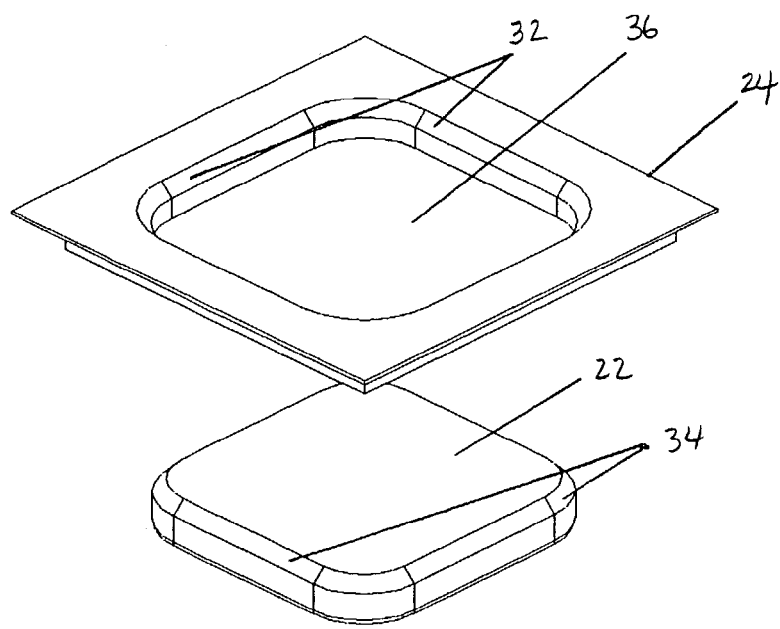
FIG. 5(b) is an exploded view of a window and frame of the assembly of FIG. 5(a)
Figure 5C:
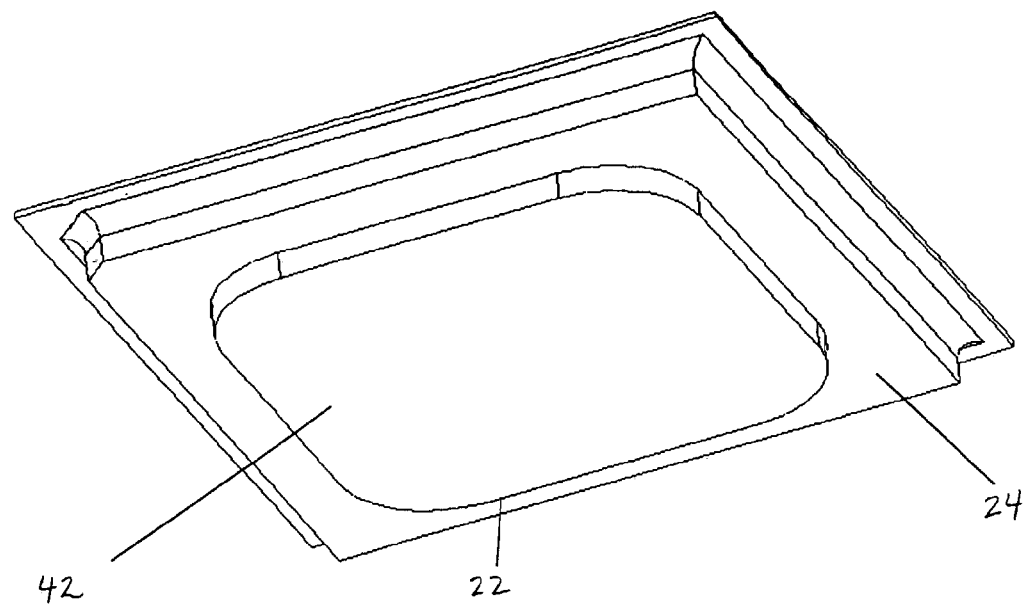
FIG. 5(c) is a bottom perspective view of the top of the window and frame of the assembly of FIG. 5(a)
Figure 5D:
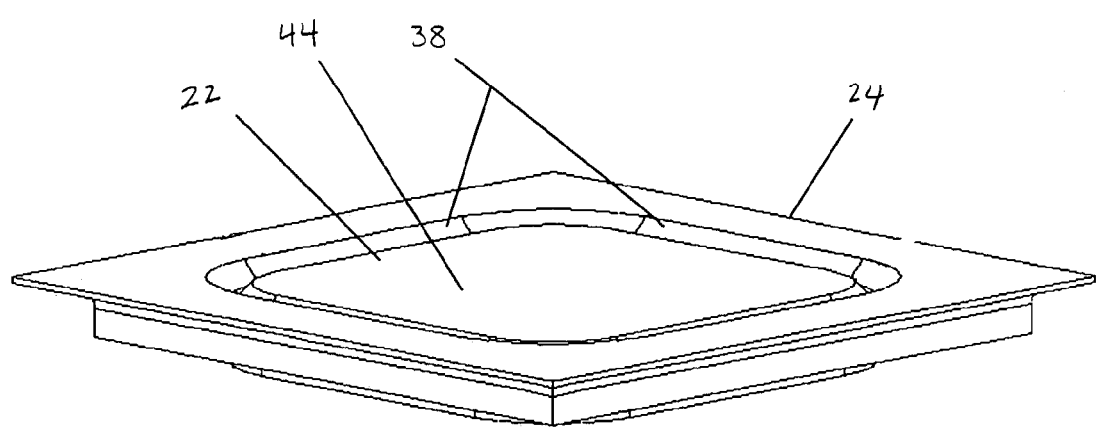
FIG. 5(d) is a top perspective view of the bottom of the window and frame of the assembly of FIG. 5(a)
Figure 5E:
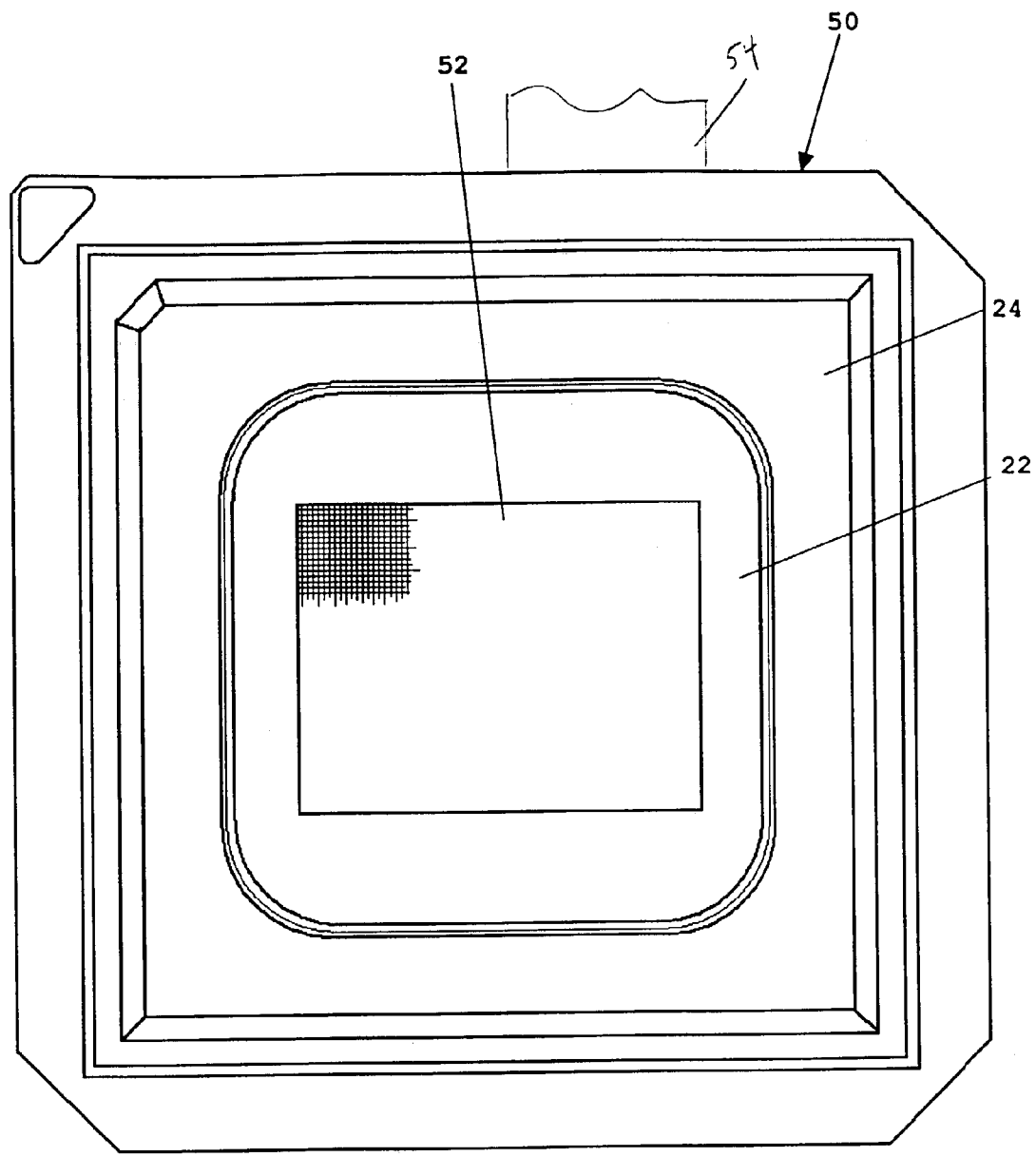
FIG. 5(e) is a plan view of a DMD provided with the window assembly of FIG. 5(a)

Turning now to FIGS. 5(a)–5(e), according to a preferred embodiment of the invention, a UV-transparent DMD window assembly 20 for a DMD™ device 50 includes a fused silica glass window 22 provided in a high temperature metal alloy frame 24. A bonding material 26 is provided at the juncture of the window 22 and the frame 24.

Figure 6:
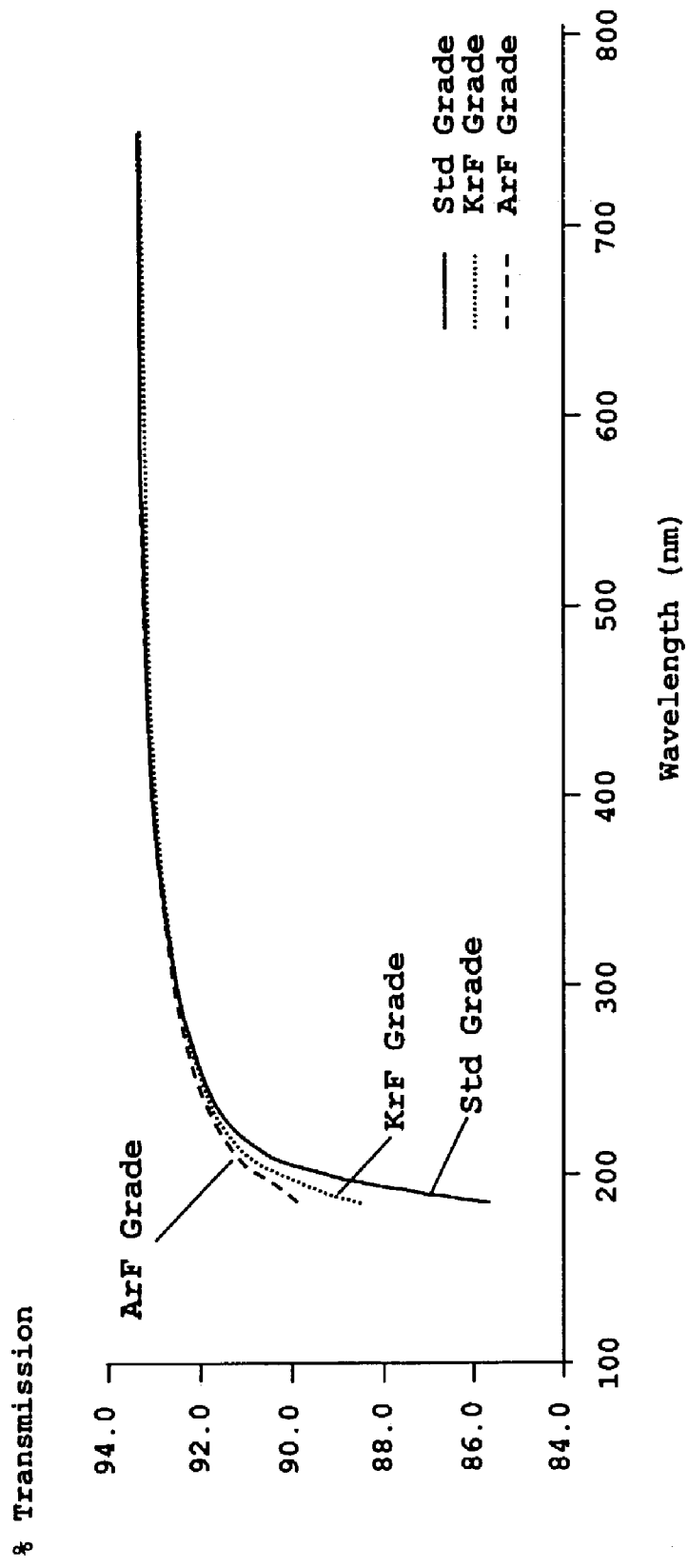
FIG. 6 shows external transmission characteristics of HPFS, Corning 7980, ArF-grade fused silica window material.

In the preferred embodiment, the fused silica glass window 22 is preferably argon fluoride (ArF) grade available from Corning (HPFS® ArF grade fused silica, Corning Code 7980). The minimum surface quality is preferably specified with a surface figure of $\lambda/10$ at 633-nm, a surface quality of 10/5 S/D (scratch/dig) and a parallelism of less than 3 arc-minutes. The base (uncoated or bare) external transmission spectrum of the ArF grade fused silica window is shown in FIG. 6. From FIG. 6, it is noted that ArF grade fused silica has at least 90% transmissibility of UV-wavelengths at 185-nm or above. Alternatively, other types of excimer grade fused silica are readily available from such companies as CVI Laser, Coherent Auburn Group, and Acton Research/Roper Scientific, and can be substituted.

The high temperature alloy for the frame 24 is preferably a nickel-cobalt-iron alloy such as Kovar® (ASTM F15), which has a composition of 29% nickel, 17% cobalt, 0.30% manganese, 0.20% silicon, 0.02% carbon, and a balance of iron.

The preferred bonding material 26 is a lead/silver alloy (approximately 97.5% lead and 2.5% silver). The lead/silver alloy is preferred because the rectangular shape (i.e., sharp corners) of the preferred window frame 24 creates stresses due to the difference in CTEs that are accommodated by the relatively ductile lead/silver alloy and, thus, helps maintain physical hold on the glass. Other lead-based alloys, such as lead/copper, lead/nickel, lead/titanium, and lead/tin can also be used. In addition, alloys of tin, including tin/silver, tin/antimony, tin/silver/copper, tin/copper, tin/silver/copper/antimony, tin/copper/antimony/silver, tin/silver/bismuth, and tin/bismuth can also be used, but generally have higher melting points (which begins to amplify the thermal expansion differences of the materials involved), are less ductile than lead-based alloys, and exhibit poor wetting of the fused silica window. Indium-bearing solders compare favorably well to lead-bearing solders in terms of ductility, melting temperature and strength and other physical properties, but are relatively expensive.

Optical coatings, discussed in detail below, are applied to the inner and outer surfaces 44, 42, respectively, of the glass window 22. Such optical coating is preferably applied by an optical coating specialty company, such as Acton Research/Roper Scientific of Acton, MA; Cleveland Crystal of Highland Heights, Ohio; or CVI Laser of Albuquerque, N.Mex., among others.

The window assembly 20 is assembled as follows. First, the high temperature metal alloy window frame 24 is constructed in a shape and size to correspond to the DMD. One reason Kovar® is the preferred material is because it can be readily machined to the exact dimensions required and also because it is the typical material for such applications. Such dimensions can be obtained from a DMD manufacturer, such as Texas Instruments. In another approach, the Kovar® frame can be obtained directly from the manufacturer. In either case, the basic frame is modified by chamfering around the bottom interior edges (at 32).

The ArF grade of fused silica window 22 is constructed in a size designed to fit in the frame 24 while allowing channel space for the intermediary lead/silver alloy brazing material, e.g., the window material is chamfered along its edge 34. When the window 22 is placed within the aperture 36 of the frame 24, the chamfered edges 32, 34 of the frame 24 and window 22 define a preferably symmetrical channel 38 which allows for the lead/silver alloy bonding material 26. In the preferred embodiment, the fused silica material 22 is arranged in a rectangular configuration (preferably with rounded corners to reduce stress), although a square (with preferably rounded corners) or circular arrangement is possible, provided that the frame 24 is machined for that shape and the resulting window aperture 36 allows light to pass to all the DMD mirrors of the mirror array 52 of the DMD 50 (FIG. 5(e)).

The window 22 is next bonded with the frame 24. To that effect, the chamfered edges 34 of the window 22 are preferably roughened and then painted with a paint containing a titanium constituent. The lead/silver brazing alloy 26 is then provided in the channel 38, and the window 22, frame 24, and brazing alloy 26 are heated together to the eutectic temperature of the brazing alloy 26 (approximately 305° C. for the preferred lead/silver alloy). During heating, a bond is formed between each of (1) the paint and the glass, (2) the paint and the lead/silver alloy and (3) the lead/silver alloy and the frame, resulting in a hermetic seal of the window to the frame. The heating may occur during or after the alloy 26 is provided into channel 38. The seal is then preferably tested for leaks using a helium leak test down to $2\times10^{-10}$ atm-cc/sec, at a pressure differential of one standard atmosphere and at 0° C.

The light transmission of window 22 is then optimized for the particular wavelength, or wavelengths, required (which will depend upon the application for which the DMD will be used) by the application of coatings, discussed below, to the outside 42 and inside 44 of the window 22. Before applying the coatings, a physical mask is preferably placed in front of the sealed window assembly to ensure the coating material does not extend beyond the window onto the frame or the alloy bond. There are several known methods for applying the coatings. In a preferred embodiment, one wavelength is selected and an anti-reflection coating is designed and applied to both surfaces of the window. For example, in the 193-nm application, the uncoated ArF-grade fused silica window has only ~4.7% reflection loss per surface (with there being front and back surfaces for each window), or about 17.5% loss in a double pass application (like the DMD application). In order to increase the window transmission, an anti-reflection (AR) coating is added thru a deposition process after the bonding process. For example, a simple magnesium fluoride ($MgF_2$) coating placed onto the outside 42 and inside 44 of the window, optimized for 193-nm and the correct angle of incidence, reduces the single surface reflection to ~1.7% at 193-nm (or an overall transmission loss of 6.63% for the double pass application) yet is still very durable to typical cleaning methods and chemicals.

The coating thickness is selected generally by starting with a λ/4 thickness ($193 \times 10^{-9}/4 = 48.25 \times 10^{-9}$ meters) for a beam striking normal to the surface. For a non-normal incident beam application, the effective difference in optical path length within the coating thickness for the non-normal incident beam must be considered. In the present application, the coating can be optimized for the exit angle (0° or normal to the window) as opposed to the entry angle (20° for a 16 micron DMD mirror (FIG. 7(a)) or 24° for a 13.7 micron DMD mirror (FIG. 7(b)). This minimizes reflections of the beam on exit of the DMD-window where it could be detrimental to have reflections bouncing between the mirrors and the inside window surface. However, ideally the AR coating should be operable over an exit angle of incidence in the range of 0° to 10° (16 micron mirror) or 0° to 12° (13.7 micron mirror), with such range improving antireflectance on the incoming beam while adequately reducing the inside reflectance.

A "cold" deposition process, such as sputtering, is preferred for application of the AR coatings. In the sputtering technique, positive energetic particles formed from a plasma bombard the target coating material and through momentum transfer sputter atoms of the target as a vapor that is then bonded to the substrate. Sputtering can produce uniform coatings over large areas, and uses the deposition material more efficiently than evaporation techniques. Other deposition techniques can be used, as long as the deposition process temperature does not reach the brazing alloy eutectic temperature. That is, deposition techniques that use high temperatures are less preferable, as such techniques may result in temperatures above the brazing alloy melting point and thus may compromise the hermetic seal.

Figure 7:
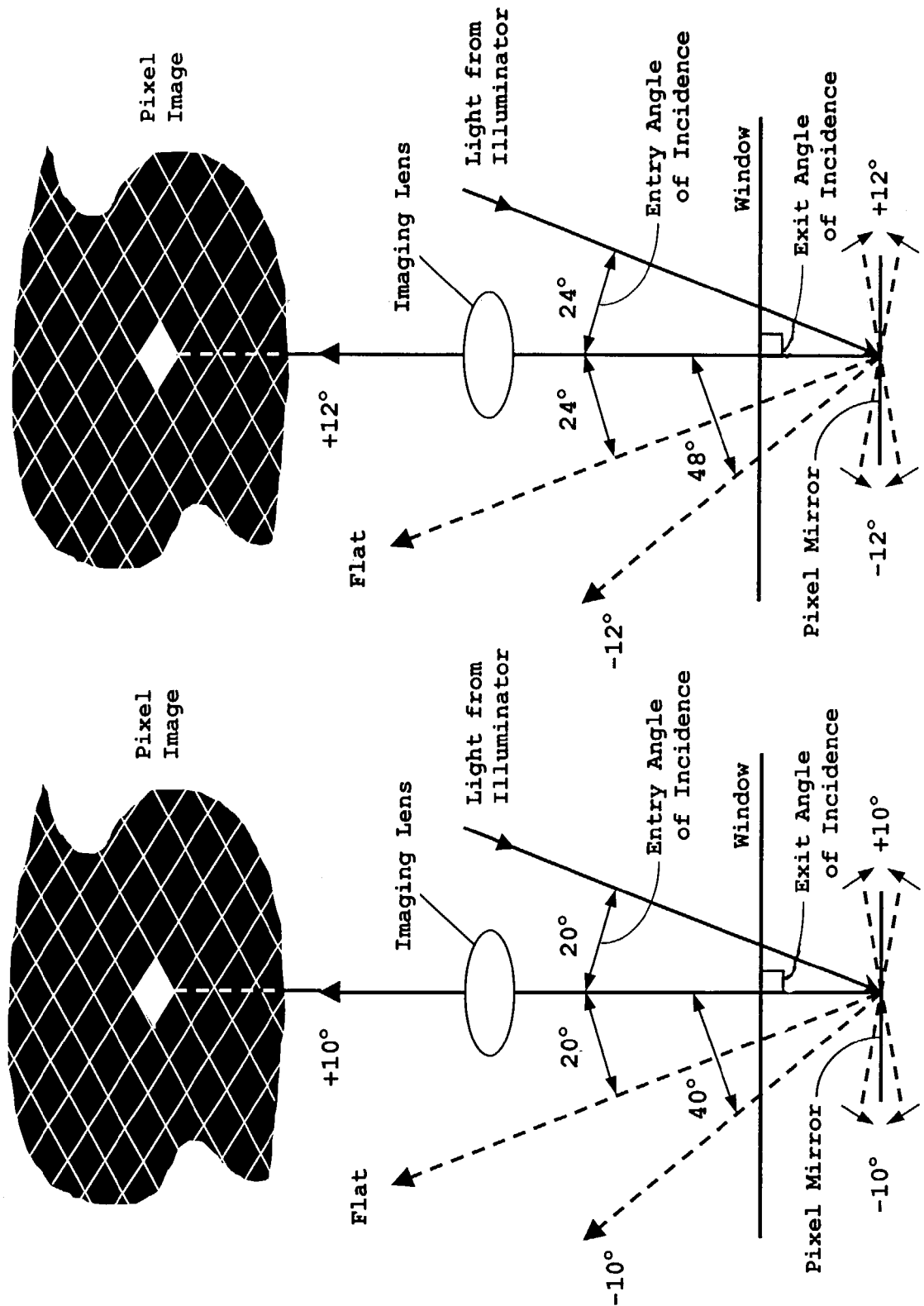
FIGS. 7(a) and 7(b) illustrate the angles-of-incidence of light entering and exiting a DMD provided with a UV-light transparent window according to the invention, where
Figure 8:
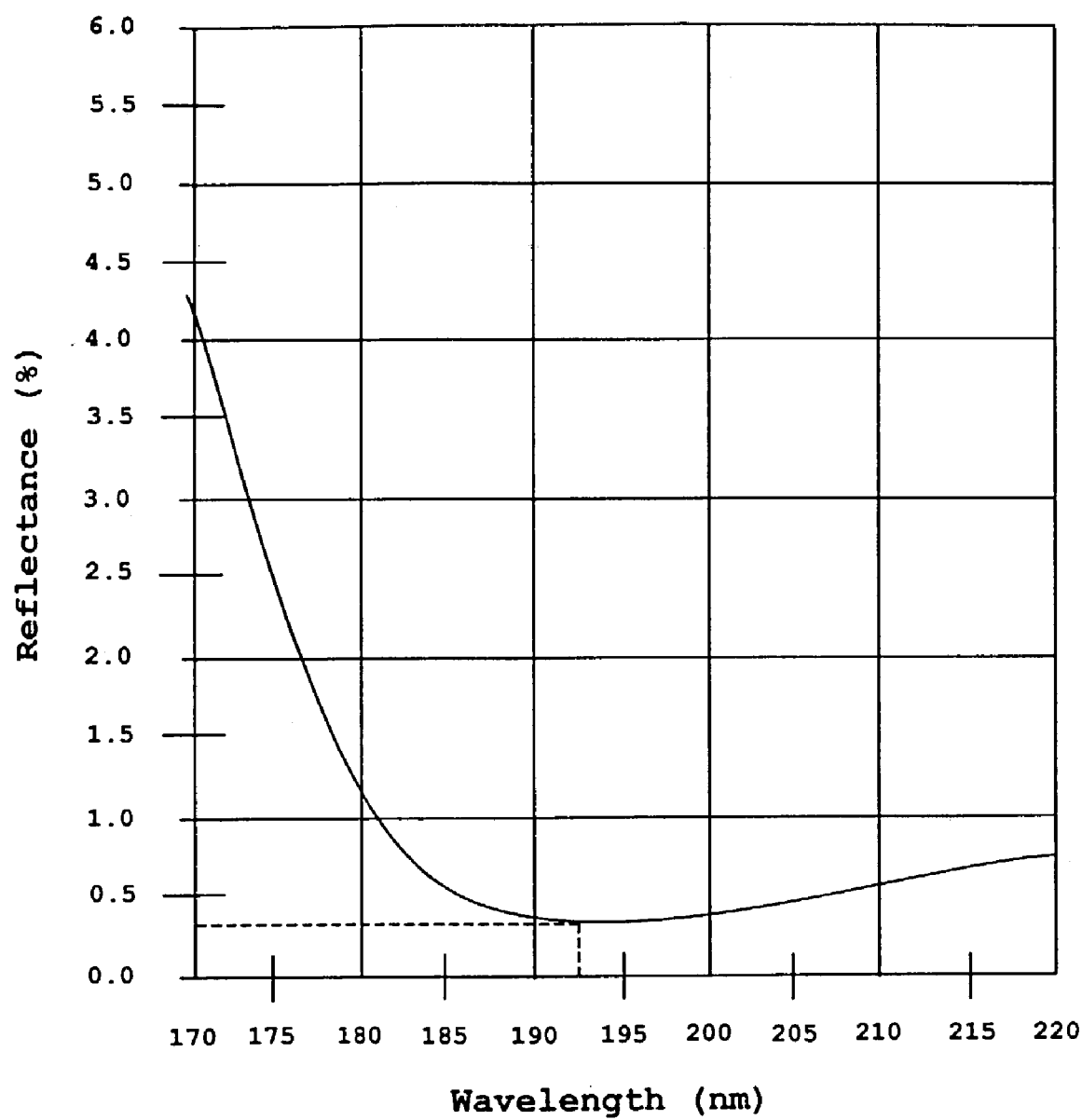
FIG. 8 shows a reflectance curve for a multiple-layer dielectric stack V-coating, optimized for a 0° or normal angle of incidence, showing less than 0.5% reflection per window surface at 193-nm.
Figure 9A:
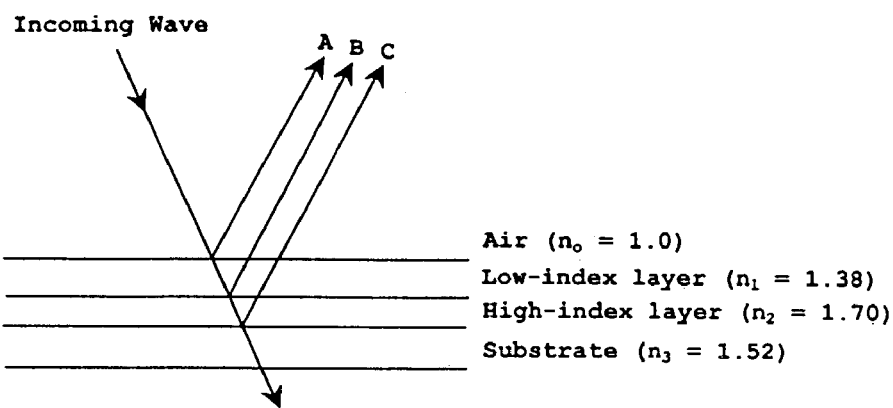
FIG. 9(a) shows a basic multi-layer AR, V-coating, optimized for a single wavelength.
Figure 9B:
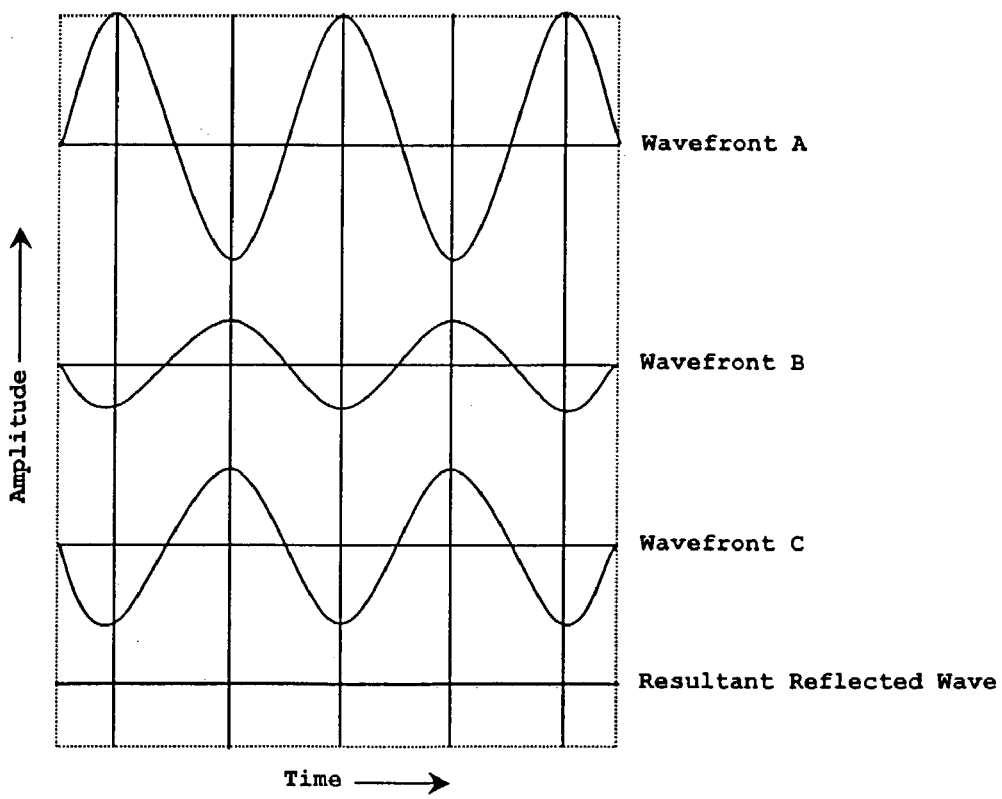
FIG. 9(b) shows destructive interference due to layers of the V-coating of FIG. 9(a)

In order to gain even more transmission, the preferred embodiment uses a multiple-layer dielectric stack coating, optimized for a 0° to 12° angle of incidence, although optimization with respect to another degree of angle-of-incidence, such as the 0° to 10° angle shown in FIG. 7(a), can be used. Such a stack coating is available from Acton Research/Roper Scientific of Acton, Mass., and offers better than 0.5% reflection (99.5% or better transmission) per window surface at 193-nm with a 0° angle of incidence (or an overall loss of 1.98% in a double pass application), as shown in FIG. 8. These narrowband antireflection (AR) coatings, often called "V" coatings, are proprietary to the coating manufacturer, e.g., materials used, number of layers, design of layer thicknesses, coating material deposition techniques, computer optimization algorithm, etc. In general, however, V-coatings are multi-layer AR coatings that reduce the reflectance of a component to near-zero for one specific wavelength. V-coatings are extremely sensitive to both wavelength and angle-of-incidence. The basic multi-layer AR V-coating, optimized for a single wavelength, is termed a quarter/quarter coating. In its simplest form, a quarter/quarter coating consists of two layers, both of which have an optical thickness of a quarter wave length at the wavelength of interest. The outer layer is made of a low-refractive-index material, and the inner layer is made of a high-refractive-index material (as compared to the substrate, such as ArF-grade fused silica). As shown in FIG. 9(a), wavefront B and wavefront C (second and third reflections, respectively) are both exactly 180-degrees out of phase with wavefront A (the first reflection). The performance of the coating is calculated in terms of the relative amplitudes and phases, which are then summed to give the overall, net amplitude of the reflected beam. In a perfect design, this result would be zero-reflectance, as indicated by the "resultant wave" in FIG. 9(b). The general example in FIGS. 9(a) and 9(b) describes a crown glass substrate with an index of refraction, $n_3$, of 1.52; a $MgF_2$ first layer with an index of refraction, $n_1$, of 1.38, and a second layer with an index of refraction, $n_2$, of 1.70 (such as beryllium oxide or magnesium oxide). The formula for exact zero reflectance for such a two layer coating at normal incidence is:

$$\frac{(n_1)^2 \cdot n_3}{(n_2)^2} = n_0$$

where no is the index of refraction of air (approximated as 1.0). In the preferred embodiment, ArF-grade fused silica is used for the 193-nm application. It has an index of refraction, $n_3$, of 1.56. Using a first $MgF_2$ layer to provide a durable protection layer, a second coating layer possessing an index of refraction of 1.72 is required in order to achieve zero reflection. Although this approach allows some freedom in the choice of coating materials and can give very low reflectance, the quarter/quarter coating can sometimes be too restrictive in the design, e.g., if a suitable coating cannot be found with the correct index of refraction, or the angle of incidence of the incoming light is not normal to the surface of the glass. For these cases, an alternative method can be used.

In the alternate method of generating a multi-layer AR coating, the layers have different thicknesses. This allows one to adjust the layers to suit the refractive index of available materials, instead of vice versa (as above). For a given combination of materials, there are usually two combinations of layer thicknesses that will give near-zero reflectance at the design wavelength. These two combinations are of different overall thickness. This method also aids in the design of coatings when the angle of incidence of the incoming light is not normal relative to the surface. However, two main issues lead to a complicated dependence of reflectance, and thus transmission, on the angle of incidence. First, the path difference of the front and rear surface reflection from any layer is a function of angle. As the angle of incidence increases from 0° relative to a normal relative to the surface, the optical path difference is decreased. The change in path difference results in a change of phase difference between two interfering reflections. Second, the reflectance of any optical interface varies according to the angle of incidence, so when combined, the phase difference between two pertinent reflections changes together with their relative amplitude. Thus, multi-layer coating design at arbitrary angles of incidence is complex. Appropriate computer modeling and optimization algorithms can be performed by optical coating companies, such as CVI Laser, Coherent Auburn Group, Melles-Griot, and Acton Research/Roper Scientific, to provide coating materials with the appropriate properties, adherence, stresses, durability, etc. In addition, the coatings can be optimized for a dual angle of incidence, such as for both (1) a 20° or 24° entry angle and (2) a 0° exit angle.

In another embodiment, the AR coating may be designed to pass dual wavelengths using the same window substrate material. For example, a simple 193-nm optimized $MgF_2$ coating placed onto one side of the ArF-grade fused silica window can reduce the single-surface reflection to ~1.7% at 193-nm and ~2.75% at 365-nm, with reflection of the wavelengths therebetween likewise substantially reduced as well. Multi-layer, dual-wavelength VV coatings can be applied to achieve even lower reflectance (more transmission) at the desired wavelengths. This generally requires additional coatings (stacks) and must be optimized with a computer algorithm by a company expert in such coatings, such as mentioned above.

Finally, the optically-coated, hermetically-sealed window unit is installed onto the DMD base in the normal manufacturing processing of the DMD semiconductor package. For example, the DMD chips are separated from the wafer, plasma cleaned, relubricated and hermetically sealed with the present invention. This is preferably performed using a parallel resistance seam welding process, although other types of semiconductor welding processes may be used. See, Hornbeck, "Digital Light Processing™ for High Brightness, High resolution Applications," *Electronic Imaging EI '97*, Projection Displays III, San Jose, Calif. (Feb. 10–12, 1997). A base 50 includes a port (not shown) at which cable 54 can be coupled to permit data transmission from a processor to the mirror array 52 to effect configuration of the mirrors in the array into desired patterns.

According to another embodiment of the invention, the window frame is constructed from a material significantly different from Kovar®. The frame material may he either silica fiber or copper/continuous-carbon-fiber alloy, which have a CTE relatively close to the UV-transmissable window material and can be machined to define the necessary shape for the DMD package. The window material can be fused silica, as previously described, or another suitable UV-transmissable material, as discussed below. The wet-bonded window and frame assembly are preferably joined using a technique such as active solder ahoy processing (e.g., S-BOND™ available from Materials Resources International in Landadale, Pa) or with low vapor epoxy to the base DMD body.

Figure 10:
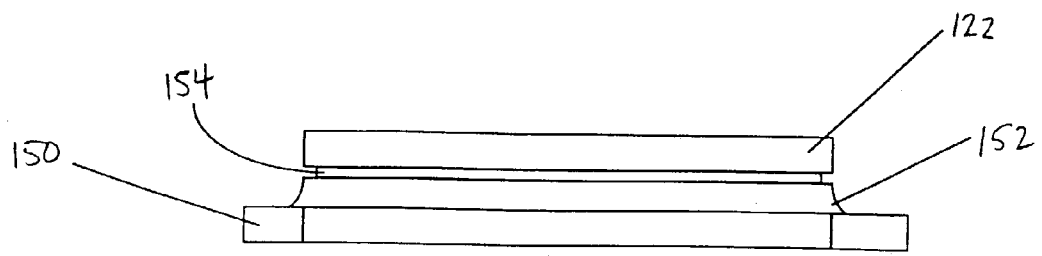
FIG. 10 is a schematic side view of a first alternate DMD assembly according to the invention.

Referring to FIG. 10, according to yet another embodiment, the window frame can be eliminated entirely, with a window 122 of appropriate size and shape bonded either directly to the DMD base 150 or to a rectangular Kovar® seal ring 152 a shoulder located on the DMD base and used in the prior art as a spacer between the DMD base and the Kovar® window frame, and as the fusing union therebetween). For example, a low vapor pressure epoxy 154 can be used to effect a seal between the window and the ceramic base of the DMD. One such suitable epoxy 154 is Tra-Bond 2116 available from Tra-Con of Bedford, Mass. Other suitable epoxies are available from Masterbond of Hackensack, N.J. While the epoxy bond may not be considered a true hermetic seal, as the bond will rarely exceed a $2\times10^{-8}$ atm-cc/sec helium leak test, the bond does meet the mil std 803 spec of less than $5\times10^{-8}$ atm-cc/sec, which is nonetheless a very good seal which is relatively easily accomplished. To effect the seal, it is preferable to mix and apply the epoxy 154, position the window 122, and uniformly press the window 122 against the DMD base 150 or seal ring 152 until the epoxy 154 is cured.

Figure 11A:
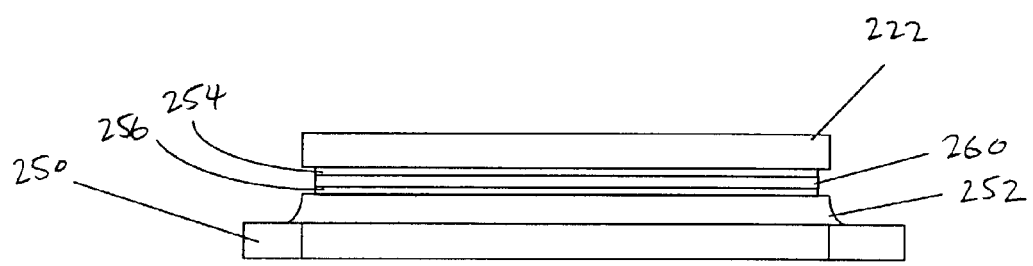
FIG. 11(a) is a schematic side view of a second alternate DMD assembly according to the invention.
Figure 11B:
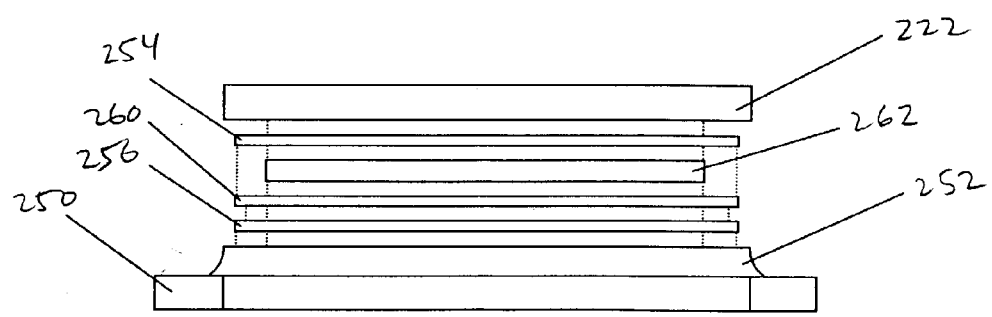
FIG. 11(b) is a schematic exploded view of the second alternate DMD assembly of FIG. 11(a)

Referring to FIGS. 11(*a*) and 11(*b*), if, based on the chosen materials, a single epoxy will not bond to both the window 222 and the DMD base 250 or seal ring 252, an intermediate material 260, such as a plastic, may be provided between the window 222 and the base 250 or the seal ring 252, with a first epoxy 254 providing a bond between the window 222 and the intermediate material 260, and a second epoxy 256 providing a bond between the intermediate material 260 and the base 250 or seal ring 252. Optionally, as discussed further below, an elastomeric o-ring 262 can be provided between the window 222 and the base 250 or seal ring 252 to effect a true hermetic seal (FIG. 11(*b*)).

Figure 12A:
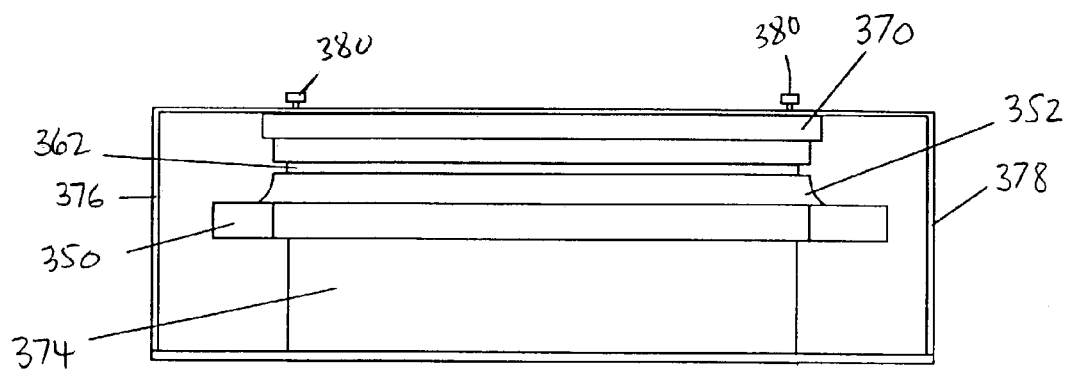
FIG. 12(a) is a schematic side view of a third alternate DMD assembly according to the invention.
Figure 12B:
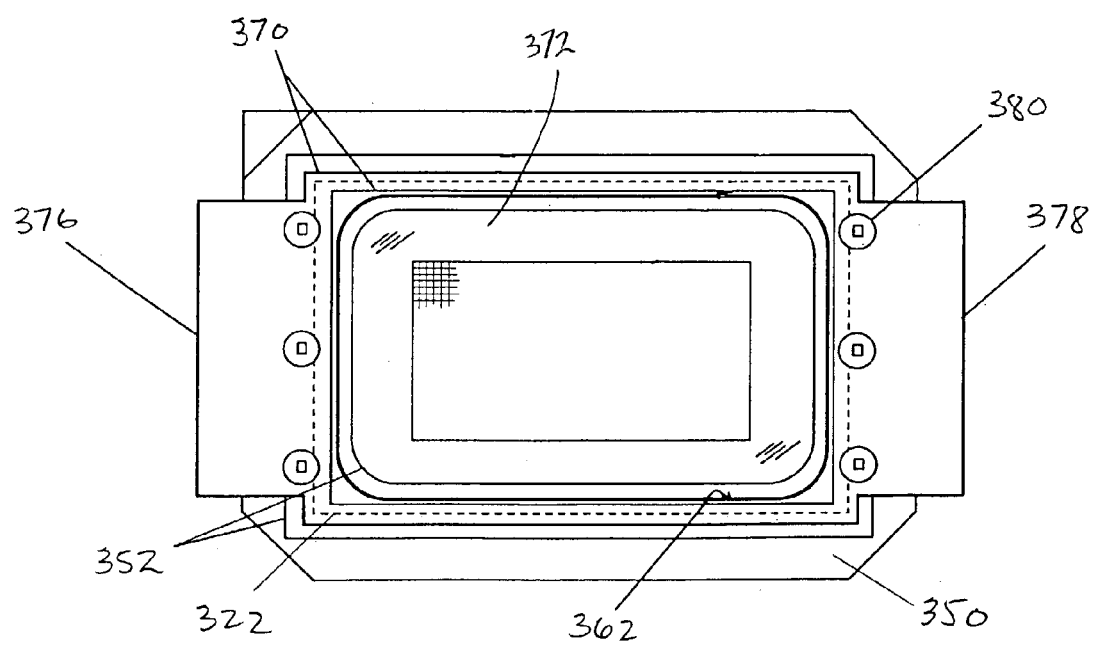
FIG. 12(b) is a schematic plan view of the third alternate embodiment of FIG. 12(a)
Figure 12C:
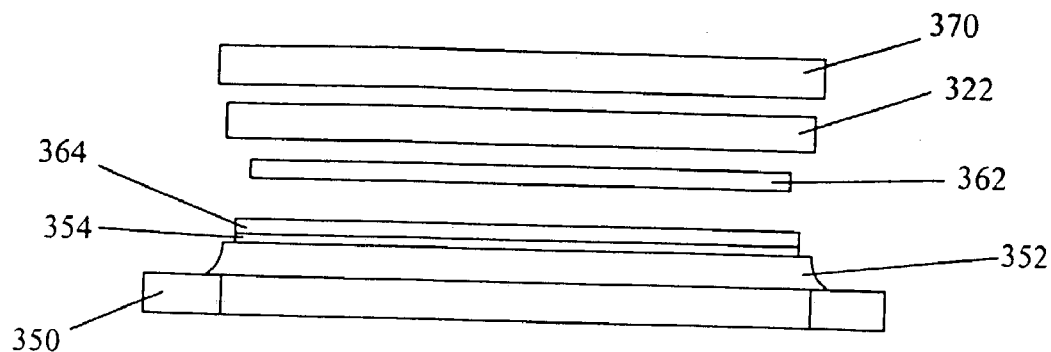
FIG. 12(c) is a schematic side view of a variation on the DMD assembly of FIG. 12(a)

Turning now to FIGS. 12(*a*) and 12(*b*), according to yet a further embodiment, the window 322 and DMD base 350 (and thus the seal ring 352) are clamped about an elastomeric seal, e.g., a vacuum grade o-ring 362, which provides a hermetic seal therebetween. Suitable elastomers include rubber, butyl, ethylene propylene, and fluorocarbon materials, such as Viton® available from DuPont Dow Elastomers. The o-ring 362 can be placed in various locations, such as on, inside, or outside the Kovar® seal ring 352. Due to the possible lack of large clamping force on the o-ring 362 (discussed further below) and/or because the existing Kovar® seal ring 352 on which the o-ring 362 may lie may not be perfectly flat, the o-ring seal may require a modification to aid in sealing.

Referring to FIG. 12(*c*), to that end, an intermediate material 364 that is extremely flat may be used over the current Kovar® seal ring 352 between the ceramic body 350 and the window 322, with the intermediate material 364 being bonded to the Kovar® seal ring 352 with low vapor epoxy 354. This approach provides a true hermetic seal. The clamping force to press the window and DMD base against the o-ring, can be effected in several ways, three of which are discussed, as follows.

First, referring still to FIGS. 12(*a*) and 12(*b*), a clamp 370 sits on the window 322 and includes a port 372 in the center thereof that allows light to pass in and out of the window 322. The DMD base 350 is coupled to a heat sink 374. The clamp 370 includes preferably two arms 376, 378 that extend in a C-shape from the front of the clamp to around back of the DMD base and preferably to the heat sink 374. Alternatively, the arms 376, 378 can extend to only the back of the base 350 of the DMD. Screws 380 are used to uniformly apply pressure across the window 322 where it contacts the o-ring 362. There are a number of different methods for carrying this out.

Still referring to FIGS. 12(*a*) and 12(*b*), according to a first assembly, the o-ring 362 is applied first, and the window 322 is properly positioned on the o-ring. Then, the clamp 370 is applied, holding the window 322 against the o-ring 362. Finally, the screws 380 are threaded relative to the clamp arms 376, 378 to pull the window 322 uniformly against the o-ring 362 to form a hermetic seal.

Figure 13A:
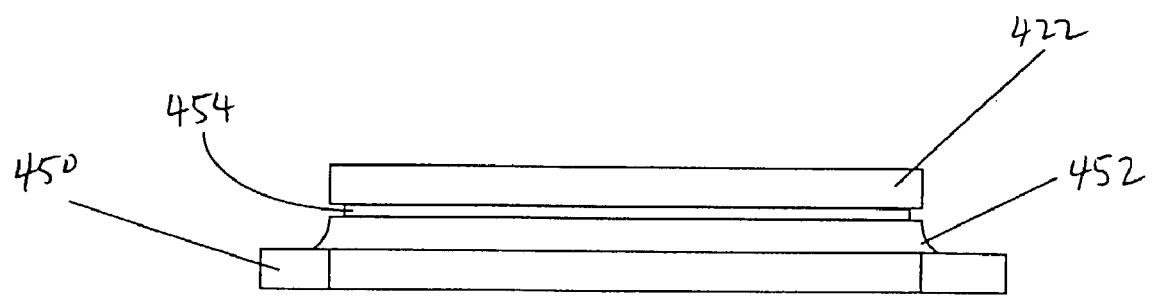
FIG. 13(a) is a schematic side view of a fourth alternate DMD assembly according to the invention.
Figure 13B:
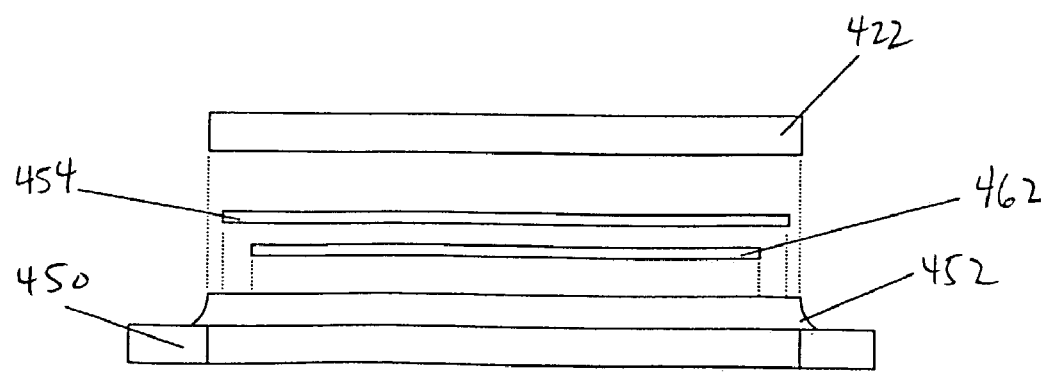
FIG. 13(b) is a schematic exploded view of the fourth alternate DMD assembly of FIG. 13(a)

Referring to FIGS. 13(*a*) and 13(*b*), according to a second assembly, the o-ring 462 is positioned on the ceramic DMD base 450 or on the seal ring 452. Next, a preferably low vapor epoxy 454 is provided on at least one of the window 422 and either the DMD base 450 or the Kovar® seal ring 452. Then, the window 422 is properly positioned on the o-ring 462. Finally, the window 422 is uniformly pressed against the o-ring 462 and epoxy 454 and held until the epoxy cures.

Figure 14:
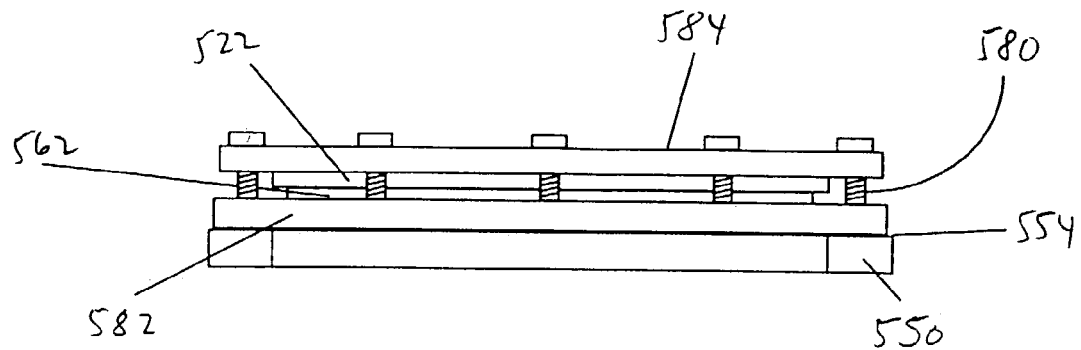
FIG. 14 is a schematic side view of a fifth alternate DMD assembly according to the invention.

Referring to FIG. 14, according to a third assembly, a metal rectangular base ring 582 is bonded to the DMD body 550 peripherally of the seal ring (not shown). The base ring 582 has a substantially flat and level upper surface with a surface area greater than the topmost surface area of the seal ring. The base ring 582 also has several tapped holes within it to accept screws. The base ring 582 is bonded with an epoxy 554 either directly onto the seal ring, directly to the ceramic body 550, or to both for added sealing capacity. The metal base ring 582 guarantees a smooth, level surface so that the o-ring 562 has a very good surface to which to adhere and to seal. There are three approaches to attaching the window 522 to the base ring 582.

In a first approach, a top metal frame 584 can be used around the window 522. The frame 584 is preferably not bonded, but simply includes a notched opening (not shown) which defines a shelf around the frame that holds the window 522. As the seal is made between the window 522 and the o-ring 562 seated on the base ring 582, this top frame 584 around the window 522 does not need to seal. The top metal frame 584 has a number of through-holes in alignment with tapped holes in the base metal ring 582. Screws 580 can be extended through the holes in the top metal frame 584, engaged with the tapped holes in the base metal ring 582, and tightened to sufficiently apply uniform pressure across the window 522.

Figure 15:
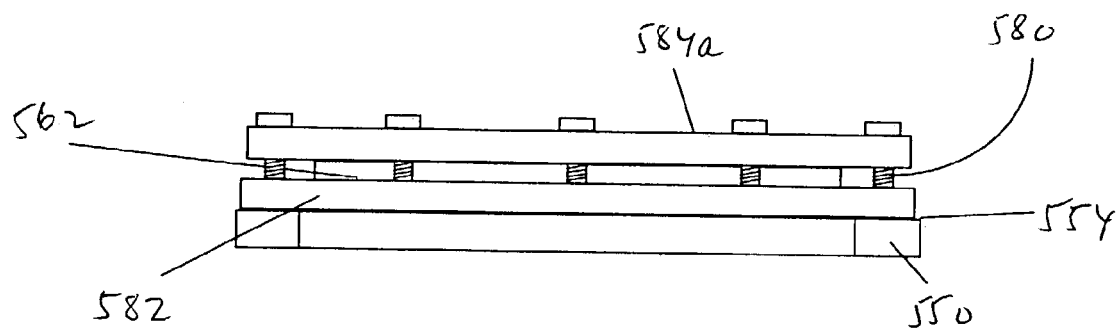
FIG. 15 is a schematic side view of a sixth alternate DMD assembly according to the invention.

Referring to FIG. 15, in a second approach, the window frame 584a is provided in a suitable alloy (other than Kovar®) or non-alloy material (e.g., ceramic) having a CTE closer to the window material. Several materials developed for semiconductor applications are particularly suitable, including silica fiber, and a copper/continuous-carbon-fiber alloy. See, e.g., Zweben, Carl, "Advanced Materials for Optoelectronic Packaging", *Electronic Packaging &Production Journal* (Sep. 1, 2002). The window 522 is bonded to the frame 584a. The frame 584a is provided with a number of holes therethrough allowing screws 580 therethrough to interface with the rectangular base ring 582 bonded to the DMD base 550 or the seal ring. In assembly, the window 522 is bonded to the frame 584a, and the base ring 582 is bonded to the DMD body 550 or seal ring using a low vapor epoxy 554. Once the epoxy 554 has cured, the o-ring 562 is positioned on the base ring 582, and the fused window/frame assembly is positioned onto the o-ring 562. Finally, the screws 580 would be inserted through the holes in the frame 584a and tightened to apply uniform window pressure against the o-ring 562.

Figure 16:
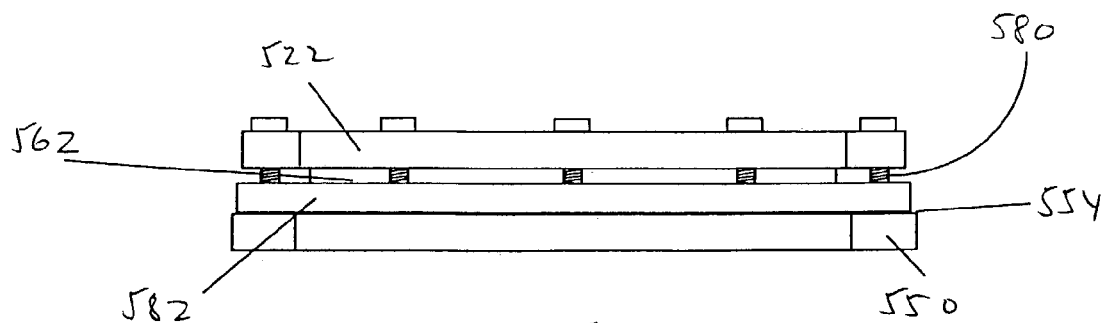
FIG. 16 is a schematic side view of a seventh alternate DMD assembly according to the invention.

Referring to FIG. 16, according to a third approach, the window 522 is provided with drilled holes and the window itself is screwed down to the base ring 582. Holes can be drilled in fused silica using diamond drill bits or with lasers. In assembly, first, holes are drilled through the window material. Second, the base ring 582 is provided with tapped holes and bonded to the DMD body 550 or seal ring using a low vapor epoxy 554. Third, once the epoxy 554 has cured, the o-ring 562 is positioned on the base ring 582. Fourth, the window 522 is properly positioned onto the o-ring 562. Finally, the screws 580 are inserted through the window holes and tightened to apply uniform pressure against the o-ring 562.

In any of the embodiments described as using an epoxy bond, an adhesive, and preferably a polymer-based adhesive, can be used in place of the epoxy. The use of adhesives permits relatively easy removal of the bonded components, if necessary.

Figure 17:
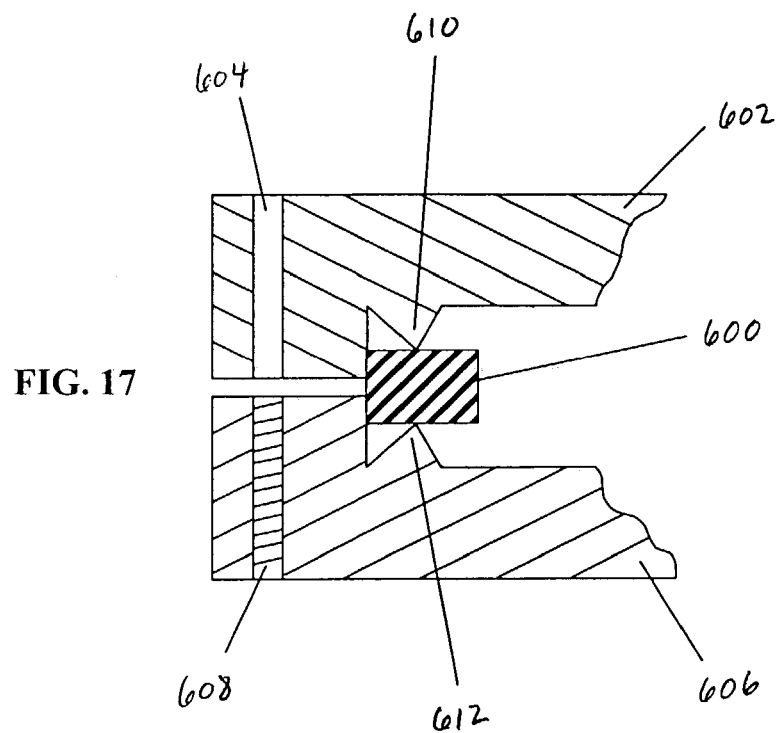
FIG. 17 is a schematic side view of an eighth alternate DMD assembly according to the invention.

There are also additional methods and materials similar to the elastomeric seal that can be used to supply excellent hermetic seals, which can be better than the elastomeric seal. Referring to FIG. 17, one such method is the knife-edge seal, which generally uses a copper or lead gasket 600, typically of a grade for vacuum compatibility. In this method, a top component (such as a frame 602 with through holes 604) and a bottom component (such as a base ring 606 with threaded holes 608) both contain knife edges 610, 612 that dig into the gasket (on both its top and bottom surfaces) as the top component is secured against the bottom component with screws (not shown). Small imperfections in the knife-edges 610, 612 are filled in with material as the gasket 600 is deformed, and a very good hermetic seal is formed.

Figure 18:
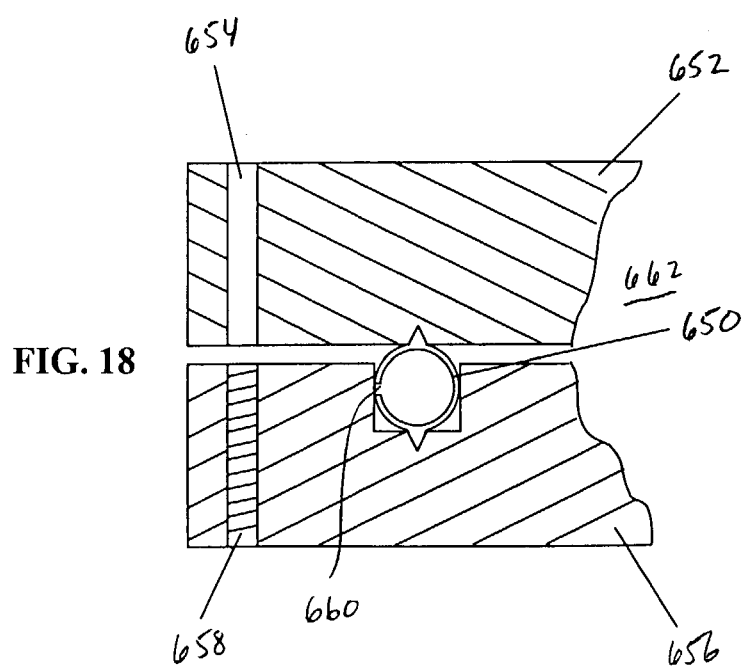
FIG. 18 is a schematic side view of an ninth alternate DMD assembly according to the invention.

Referring to FIG. 18, another method is known generically as the C-seal, whereby a C-shaped material 650 is used to provide the seal between two opposing components (such as a top frame 652 with through holes 654 and a bottom base ring 656 with threaded holes 658). In a classic "C" seal the open side 660 of the "C" 650 faces away from the sealed environment 662. The seal compresses slightly when the joint is made up, e.g., the top component is secured against the bottom component with screws (not shown). The elastic properties of the seal material maintain pressure against the surfaces of the sealing cavity. The seal material is softer than the cavity surface. The softer seal material fills imperfections in the cavity surface to create a leak-tight joint. There are further variations on this method, which supply even greater sealing capacity, such as an "energized" C-seal. Such seals, often termed Helioflex seals, are available from Garlock Helicoflex, Columbia, S.C.

Referring to yet another aspect of the invention, the mirrors on the DMD base are preferably coated with a high reflectance (HR) coating adapted to enhance UV-light reflection relative to the uncoated typically aluminum mirrors. The HR coating is preferably adapted for a 10° to 30° or 12° to 36° angle of incidence (depending upon mirror size). In the "ON" position, the mirror is tilted toward the incoming illumination by 10° or 12°. Thus, the illumination will strike the mirrors at either 10° or 12°. Most maximum HR reflection coatings consist of dielectric materials which yield narrow bands of high reflectance at particular wavelengths. HR dielectric layers work on the same principles as dielectric anti-reflection coatings. Quarter-wave thicknesses of alternately high- and low-refractive index materials are applied to the aluminum mirror substrate to form a dielectric multilayer. By choosing materials of appropriate refractive indices, the various reflected wavefronts can be made to interfere constructively in order to produce a highly efficient reflector. The peak reflectance value is dependent upon the ratio of refractive indices of the two materials, as well as the number of layer pairs. Increasing either increases the reflectance. An optimized coating at 10° or 12° angle of incidence reflection is 97% to 99% at 193-nm (or a loss of only 1 to 3%) and 90% to 95% at 157-nm (or a loss of only 5 to 10%). As the angle of incidence increases from 10° or 12°, the reflectance decreases. However, such losses are minimal for the full range of movement of the mirrors. Additionally, a simple magnesium fluoride coating deposited on the bare aluminum mirror will provide a broadband reflection in the 157-nm to 193-nm range of 86% to 88%, thus providing more of a general-purpose approach, but with reduced reflection overall. This may be acceptable in some applications.

The HR coatings can be applied during manufacture of the DMD, or after the DMD has been manufactured, but before the window has been applied. To apply the HR coating during the manufacture of the DMD, a completed CMOS memory circuit (an SRAM cell) for the DMD superstructure is obtained, and an interlevel dielectric is provided over the metal-2 layer of the CMOS. The dielectric is then planarized using a chemical mechanical polish (CMP) technique which provides a completely flat substrate for DMD superstructure fabrication. Through the use of several photomask layers, the superstructure is formed with layers of aluminum and proprietary metal alloys for the address electrode (metal-3), hinge, yoke and mirror layers and hardened photo-resist for the sacrificial layers (spacer-1 and spacer-2) that form the air gaps. The aluminum and metal alloys are sputter-deposited and plasma-etched using plasma-deposited $SiO_2$ as the etch mask. Later in the packaging flow, the sacrificial layers are plasma-etched to form the air gaps. The HR coating is preferably deposited after the aluminum mirror layer is deposited, and before the sacrificial layers are etched.

Figure 19:
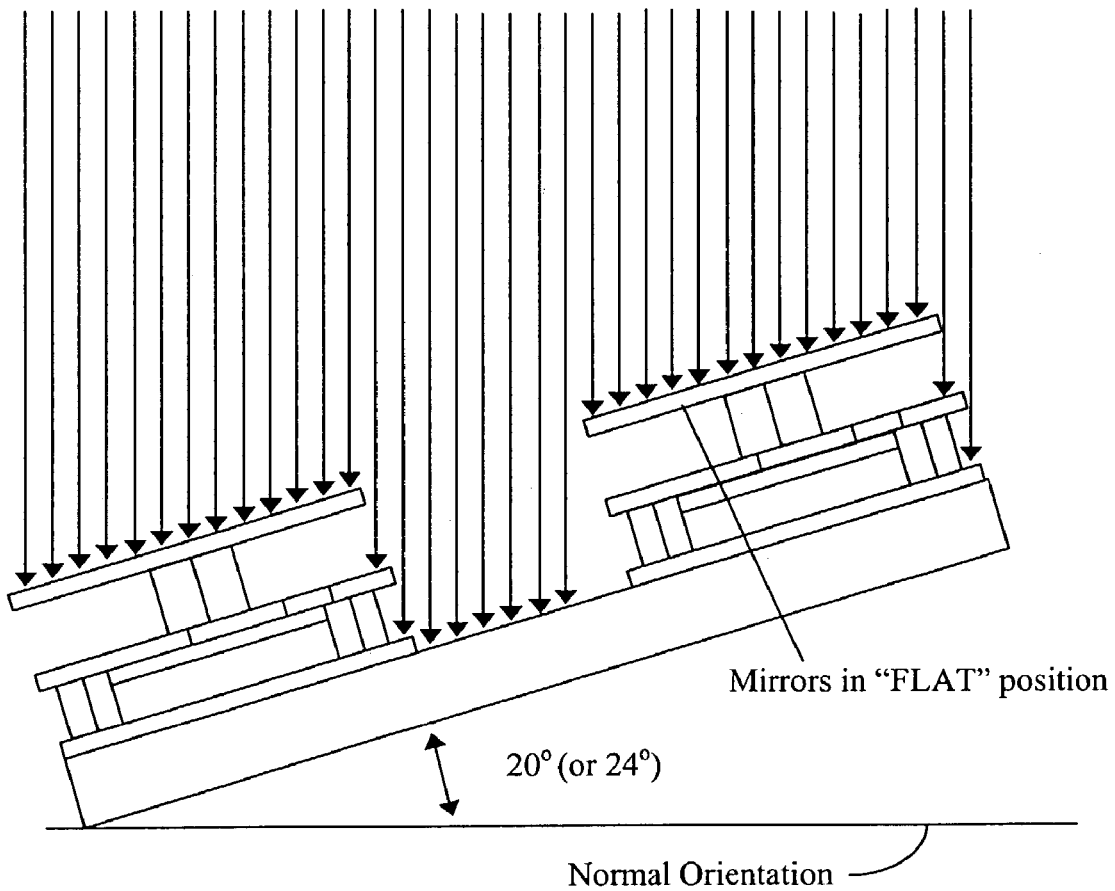
FIG. 19 illustrates high reflectance (HR) coating of the DMD mirrors and underlying structure.

In the second method, the HR coating is applied after the DMD has been manufactured but before the UV-window is applied. Referring to FIG. 19, during the coating process, the micromirrors are preferably in their "flat" state, and the DMD unit is rotated to match the angle of the incoming laser beam (e.g., 20° for a 16-micron mirror package and 24° for a 13.7-micron mirror package). This allows coating of the underlying structure behind the mirrors, thus protecting these structures from the UV energy. The HR coating is applied preferably using a cold deposition technique, such as sputtering. The UV-window, in one of its many possible embodiments, is then attached to the DMD unit.

OTHER APPLICATIONS

There are other applications where the deep-UV DMD window assembly of the invention can be used. The DMD is an ideal device for delivering patterns to semiconductor material, or other material, in the production of integrated circuits (IC), or other optical lithography applications (such as polymer arrays). Currently, expensive, non-changeable, photomasks are used to provide the deprotection patterns for the etching process. Photomasks, requiring sophisticated manufacturing techniques and complex mathematical algorithms to design, are at the forefront of the microminiaturization of chips, enabling more functionality to be embedded within a smaller area. Photomasks are an integral component in the lithographic process of semiconductor manufacturing. They consist of high-purity quartz or glass plates containing precision patterns of integrated circuits, and are used as masters by chipmakers, and other industries, to optically transfer these images onto semiconductor wafers. Current advanced lithographic tools, such as deep-UV steppers, project light through a photomask and a high aperture lens. The predominant light wavelengths are 248-nm and 193-nm, although, as discussed below, 157-nm wavelengths are beginning to emerge. The intensity of the light casts an image of the design for the device (i.e., the pattern on the photomask) onto a silicon wafer coated with a light sensitive material called photoresist. Using negative photoresist the unexposed, or masked, portion of this material is then removed so it can either be etched to form channels or be deposited with other materials. The process is reversed using positive photoresist. ICs are manufactured layer by layer, so these selective deposition/removal steps are repeated until the circuit is built. The current generation of semiconductors often has twenty-five or more layers, each requiring a unique photomask.

With the use of a DMD, the photomask is eliminated as the desired pattern can be readily implemented on the DMD mirror array, provided the DMD has the necessary resolution. Using the appropriate light, the DMD mirrors can then cast, or direct, the image onto the silicon wafer substrate, or other material, coated with the light-sensitive photoresist. Since the host computer controls the DMD mirrors, the pattern can be changed rapidly by turning the appropriate mirrors ON or OFF. The masked portion of this material is then removed so it can either be etched to form channels or be deposited with other materials. Presently, the DMD is not being used in these vacuum-UV and deep-UV applications largely due to the current, commercially-available, UV-limited DMD window design. The UV-transmissable DMD window of the present invention in this patent can allow the use of the DMD in these applications.

In addition, optical lithography with 157-nm fluorine lasers is rapidly emerging as a viable technology for the post-193-nm era. In fact, it may become the technology of choice for 100-nm to 70-nm nodes (i.e., small physical details). It is attractive for several reasons, the most important being that it is fundamentally an extension of optical lithography at the longer wavelengths of 248 and 193 nm. Therefore, it holds the promise that the tool-manufacturing and wafer-processing infrastructures can be adapted to it relatively easily, and that optical-resolution-enhancing techniques (phase-shifting masks, off-axis illumination, etc.) can be applied to it as well. However, this approach still uses photomasks as described above for the 248-nm and 193-nm wavelengths. Thus, a window for the DMD allowing the transmission of 157-nm would be advantageous as semiconductor processing moves in this direction.

The main difference between the main window embodiment and the deeper UV wavelength windows (such as down to 157-nm and even below) is the window material and coatings used for the shorter wavelengths. Currently, a preferred optical material for the window in vacuum-UV (VUV, generally defined as 100-nm to 200-nm) applications is lens-quality calcium fluoride ($CaF_2$) (having a transmission of at least 50% for wavelengths down to 130-nm), particularly as disclosed in U.S. Pat. No. 6,242,136 to Moore et al., which is hereby incorporated by reference herein its entirety. Other candidate materials include barium fluoride ($BaF_2$) (having a transmission of at least 50% for wavelengths down to 150-nm), strontium fluoride ($SrF_2$) (having a transmission of at least 50% for wavelengths down to 140-nm), lithium fluoride (LiF) (having a transmission of at least 70% for wavelengths down to 120-nm), magnesium fluoride ($MgF_2$)(having a transmission of at least 65% for wavelengths down to 120-nm), and sodium. fluoride (NaF) (having a transmission of at least 50% for wavelengths down to 135-nm). The bonding of the window to the frame is similar to that described in the above described embodiments, although the bonding alloy may have different properties.

To optimize transmission for the 157-nm wavelength, fluorides are a preferred coating, as most oxide compounds (such as silicon dioxide or hafnium oxide) are too absorptive at 157-nm. For example, low index of refraction materials may include magnesium fluoride and aluminum fluoride, while high index materials may include lanthanum fluoride and gadolinium fluoride. Coating design and application techniques are very similar to those discussed above.

There have been described and illustrated herein embodiments of (i) a DMD, (ii) UV-transmissable window assemblies therefor, and (iii) methods for constructing the same. While particular embodiments of the invention have been described, it is not intended that the invention be limited thereto, as it is intended that the invention be as broad in scope as the art will allow and that the specification be read likewise. Thus, it is recognized that DMD windows for other UV wavelengths can be constructed by the above method by using appropriate materials for those particular wavelengths.

Furthermore, while the invention has been described particularly with respect to a DMD, it is recognized that the UV-transmissable window assemblies may have application in optical MEMS devices, such as deformable and active mirror devices. It will also be appreciated by those skilled in the art that yet other modifications could be made to the provided invention without deviating from its spirit and scope as claimed.

What is claimed is:

1. A digital micromirror device (DMD), comprising:
   a) a base element having a first side and a second side, said first side provided with a two dimensional array of individually addressable mirrors;
   b) a heat sink coupled said second side of said base element;
   c) a frame having an aperture at least the size of the mirror army;
   d) a window between said frame and said base element, said window comprising a material adapted to permit at least 90% transmissibility of UV wavelengths at 185-nm and above;
   e) a plurality of clamping arms extending about said frame and said heat sink such that said window is clamped between said frame and said base element with a clamping force; and
   f) an elastomeric o-ring sealing element situated between said window and said base element, wherein said clamping force and said sealing element effect a hermetic seal between said window and said base clement.

2. A DMD according to claim 1, wherein:
said first side of said base element is provided with an upstanding ring structure, and said sealing element is provided at least partially within said ring structure.

3. A DMD according to claim 2, wherein:
said ring structure is constructed of Kovar® alloy.

4. A DMD according to claim 1, further comprising:
an epoxy bonding said window to said base.

5. A DMD according to claim 4, wherein:
said epoxy is a low vapor epoxy.

6. A DMD according to claim 1, further comprising:
an epoxy,
   wherein said first side of said base element is provided with an upstanding ring structure, and said epoxy bonds said window to said ring structure.

7. A DMD according to claim 1, wherein:
said clamping force is effected with screws extending through said frame.

8. A DMD according to claim 1, herein:
said sealing element is made from vacuum grade rubber.

9. A DMD according to claim 1, herein:
exactly two arms are provided.

10. A DMD according to claim 1, wherein:
said frame is made from Kovar® alloy.

11. A DMD according to claim 1, wherein:
said window comprises fused silica.

12. A DMD according to claim 1, wherein:
said window comprises argon fluoride grade fused silica.

13. A digital micromirror device (DMD), comprising:
a) a base element having a first side and a second side, said first side provided with a two dimensional array of individually addressable mirrors;
b) a frame having an aperture at least the size of the mirror array;
c) a window between said frame and said base element, said window comprising a material adapted to permit at least 90% transmissibility of UV wavelengths at 185-nm and above;
d) a plurality of clamping arms extending about said frame and said second side of said base element such that said window is clamped between said frame and said base element with a clamping force;
e) an elastomeric element situated between said window and said base element, wherein said clamping force and said elastomeric element effect a hermetic seal about said array of mirrors;
f an upstanding ring structure on said first side of said base element situated between said base element and said window, said upstanding ring having a topmost portion with a first surface area; and
g) an outer base ring having a substantially flat upper surface with a second surface area greater than said first surface area, said base ring bonded to at least one of
   (i) said upstanding ring structure, and
   (ii) said base element about said upstanding ring structure,
   wherein said window is bonded to said second surface of said base ring.

14. A DMD according to claim 13, wherein:
said sealing element is constructed from one of rubber, butyl, ethylene propylene, and a fluorocarbon.

15. A DMD according to claim 13 wherein:
said base ring is bonded with a low vapor epoxy.

16. A DMD according to claim 13 wherein:
said second surface is level.

17. A DMD according to claim 13, wherein:
said second surface is substantially flat.

18. A DMD according to claim 13, wherein:
said frame is made of one of an alloy and a ceramic.

19. A digital micromirror device (DMD), comprising:
a) a base element having a first side and a second side, said first side provided with a two dimensional array of individually addressable mirrors;
b) a window over said base element, said window comprising a material adapted to permit at least 80% transmissibility of UV wavelengths at 185-nm and above;
c) an epoxy bond between said window and said base element; and
d) an elastomeric o-ring situated between said window and said first side of said base element.

20. A DMD according to claim 19 wherein:
said window and said base element are coupled together, and said coupling and said o-ring provide a hermetic seal about said array of mirrors.

21. A DMD according to claim 19, wherein:
said window is coupled to said base with screws.

22. A DMD according to claim 19, wherein:
said window is chosen to provide at least 50% transmission of light waves at and above 130-nm.

23. A DMD according to claim 19, wherein:
said window is chosen to provide at least 65% transmission of light waves at and above 120-nm.

24. A digital micromirror device (DMD), comprising:
a) a base having a first side and a second side, said first side provided with a two dimensional array of individually addressable mirrors and a metal allay seal ring about said array of mirrors;
b) a window over said seal ring, said window comprising a material adapted to permit at least 80% transmissibility of UV wavelengths at 1 85-nm and above;
c) an epoxy bond between said window and at least one of said seal ring and said base; and
d) an elastomeric o-ring situated between said window and at least one of said seal ring and said base.

25. A digital micromirror device (DMD), comprising:
a) a base having a first side and a second side, said first side provided with a two dimensional array of individually addressable minors;
b) a window coupled to said base wit screws, said window comprising a material adapted to permit at least 80% transmissibility of UV wavelengths at 185-nm and above; and
c) an elastomeric o-ring situated between said window and said first side of said base.

26. A digital micromirror device (DMD), comprising:
a) a base element having a first side and a second side, said first side provided with a two dimensional array of individually addressable mirrors;
b) a window comprising a material adapted to permit at least 80% transmissibility of UV wavelengths at 185-nm and above; and
c) a frame bonded to both said window and said base element, wherein said frame is constructed of a material having a CTE closer to the window material than $5.2 \times 10^{-31}/°C$.

27. A digital micromirror device (DMD), comprising:
a) a base element having a first side and a second side, said first side provided with a two dimensional array of individually addressable mirrors;
b) a base ring on said base element and about said array of mirrors;
c) a window comprising a material adapted to permit at least 80% transmissibility of UV wavelengths at 185-nm and above; and
d) a frame about said window; and
e) a gasket between said base ring and said frame.

28. A DMD) according to claim 27, wherein:
said base ring, said frame and said gasket together define a knife edge seal.

29. A DMD) according to claim 28, wherein:
said gasket is made of one of copper and lead.

30. A DMD according to claim 29, wherein:
said gasket has a C-shaped cross-section.

* * * * *